(12) United States Patent
Thompson et al.

(10) Patent No.: US 6,696,241 B2
(45) Date of Patent: Feb. 24, 2004

(54) MEASURING ESTERASE ACTIVITY USING FLUORESCENT SUBSTRATES AS A WAY OF EVALUATING CERVICAL CANCER

(75) Inventors: James Thompson, Ladera Ranch, CA (US); Weidong Huang, Torrance, CA (US)

(73) Assignee: The Regent of the University of California, Oakland, CA (US)

( * ) Notice: Subject to any disclaimer, the term of this patent is extended or adjusted under 35 U.S.C. 154(b) by 0 days.

(21) Appl. No.: 09/755,880

(22) Filed: Jan. 4, 2001

(65) Prior Publication Data

US 2001/0049091 A1 Dec. 6, 2001

Related U.S. Application Data

(63) Continuation of application No. PCT/US99/15401, filed on Jul. 8, 1999.
(60) Provisional application No. 60/092,210, filed on Jul. 8, 1998.

(51) Int. Cl.$^7$ .................. C12Q 1/00; G01N 33/567; G01N 33/574; G01N 33/573; G01N 33/53

(52) U.S. Cl. .................. 435/4; 435/7.21; 435/7.23; 435/7.4; 435/7.92; 435/325; 436/63; 436/64; 436/164; 436/166; 436/172; 436/174

(58) Field of Search .................. 435/4, 7.21, 7.23, 435/7.4, 7.92, 325.1; 436/63, 64, 164, 166, 172, 174

(56) References Cited

U.S. PATENT DOCUMENTS

| | | |
|---|---|---|
| 5,635,402 A | 6/1997 | Alfano et al. |
| 5,698,411 A | 12/1997 | Lucas et al. |
| 5,733,719 A | 3/1998 | Jaffe et al. |
| 5,776,720 A | 7/1998 | Jaffe et al. |
| 5,849,513 A | 12/1998 | Jaffe et al. |
| 5,871,946 A | 2/1999 | Lucas et al. |
| 5,905,031 A | 5/1999 | Kuylen et al. |
| 5,976,822 A | 11/1999 | Landrum et al. |

OTHER PUBLICATIONS

Watson et al. A Flow Cytofluorimetric method for measuring enzyme reaction kinetics in intact cells. FEBS Letters 81(1): 179–182, Sep. 1977.*
Aoki et al. (1981) "Carbamoyl Phosphate Synthetase (Glutamine–Hydrolyzing): Increased Activity in Cancer Cells", *Science* 212:463–5.
Boekhorst et al. (1993) Enhanced Chemosensitivity in Acute Myeloid Leukemia by Hematopoietic Growth Factors: a Comparison of the MTT Assay with a Clonogenic.
Burger et al. (1996) "Human Papillomavirus Type 18: Association With Poor Prognois in Early Stage Cervical Cancer", *J. Natl. Cancer Inst.* 88:1361–8.

Chiba et al. (1995) "A correlation study between serum adenosine deaminase activities and peripheral lymphocyte subsets in Parkinson's disease", *J. Neurol. Sci.* 132:170–173.
Chomette et al. (1984) "Histoenzymological features of epithelial cells in epidermoid carcinomas of oral mucosa and in amelobastomas of jaws", *Pathol Biol* 32:995–1003.
Cohn et al. (1997) "The Significance of Allelic Deletions and Aneuploidy in Colorectal Carcinoma", *Cancer* 79:233–244.
Cook et al. (1994) "Flow cytometric measurement of non–specific esterase activity", *J. Immunol. Methods* 168:203.
Davey (1997) "Quality and Liability Issues with the Papanicolaou Smear" *Arch. Pathol. Lab. Med.* 121:267–9.
DeMay (1997) "Common Problems in Papanicolaou Smear Interpretation", *Arch. Pathol. Lab. Med.* 121:229–38.
Eskandari et al. (1977) "Lipopolysaccharide activates the muscularis macrophage network and suppresses circular smooth muscle activity" *Am. J. Physiol.* 273:727–734.
Flanigan et al. (1986) "Proliferation, Esterase Activity, and Propidium Iodide Exclusion in Urologic Tumor Cells After In Vitro Exposure to Chemotherapeutic agents". *J. Urol.*
Giaretti et al. (1996) "Intratumor Heterogeneity of K–ras2 Mutations in Colorectal Adenocarcinomas", *Am. J. Pathol.* 149:237–245.
Kamarck (1987) "Fluorescense–Activated Cell Sorting of hybrid and Transfected Cells", *Methods Enz.* 151:150–165.
Kashimura et al. (1993) "Problems in Papanicolaou classification", *J. UOEH*, 15:37–43.
Klemm et al. (1996) "Cervical Cancer: A Developmental Perspective", *J. Obstet. Gynecol. Neonatal Nurs.* 25:629–634.
Kondo et al. (1984) "Rationale for a Novel Immunology of Cancer with Allogeneic Lymphocyte Infusion", *Med. Hypotheses* 15:241–77.
Kruse et al. (1990) Analysis of interleukin 2 and various effector cell populations in adoptive immunotherapy of 9L rat gliosarcoma: Allogeneic cytotoxic T lymphocytes.
Kruse et al. (1994) "Intracranial administrations of single or multiple source allogeneic cytotoxic T lymphocytes: chronic therapy for primary brain tumors", *J. Neuro–Oncol.*
Kurtycz et al. (1996) "Use of Fluorescent In Situ Hybridization to Detect Aneuploidy in Cervical Dysplasia", *Diagn. Cytopathol.* 15:46–51.

(List continued on next page.)

*Primary Examiner*—Alana M. Harris
(74) *Attorney, Agent, or Firm*—Carol L. Francis; Bozicevic, Field & Francis, LLP (57) ABSTRACT

The present invention provides methods of determining whether test cells in a sample are cancerous or not and determining if lymphocytes are activated or not. The method measures the test cell's DNA ploidy and the cellular activity of an enzyme such as an esterase, which has altered expression in cancer cells. Esterase activity can be measured using fluorescent compounds such as fluorescein diacetate.

14 Claims, 2 Drawing Sheets

OTHER PUBLICATIONS

La Porta et al. (1997) Changes in protein kinase $C_\alpha$ $\delta$ and in nuclear $\beta$ isoform expression in tumour and lung metastatic nodules induced by diethylnitrosamine in the.

Lieu (1996) "The Papanicolaou Smear: Its Value and Limitations", *J. Fam. Pract.* 42:391–399.

Liewald et al. (1992) "Prognostic value of flow cytometrically determined DNA–ploidy, intracellular pH and esterase activity of non–small cell lung carcinomas", *Anal. Cell. Pathol.*

Miller et al. (1992) "Evaluation and Follow–up of Abnormal Pap Smears", *Am. Fam. Phys.* 45:143–150.

Mitchell et al. (1995) "Differences between Papanicolaou smears with Correct and Incorrect diagnoses", *Cytopath.* 6:368–75.

Naryshkin (1997) "The False–Negative Fraction for Papanicolaou Smears", *Arch. Pathol. Lab. Med.* 121:270–272.

Nenning et al. (1995) "False positive cervical smears: a cytometric and histological study", *Anal. Cell. Pathol.* 9:61–8.

Neubauer et al. (1989) Flow–cytometric determination of intracellular pH, esterase activity and cell volume in human leukemic cell lines following in vitro incubation with.

Norazmi et al. (1995) "Increased level of activated $_\gamma\delta$ lymphocytes correlates with disease severity in HIV infection", *Immunol. Cell. Biol.* 73:245–248.

Oosterhuis et al. (1991) "Mediastinal Germ Cell Tumor with Secondary Nongerm Cell Malignancy, and Extensive Hematopoietic Activity", *Cancer Genet. Cytogenet.* 54:183–95.

Pardoll et al. (1992) "New strategies for active immunotherapy with genetically engineered tumor cells", *Curr. Opin. Immunol.* 4:619–623.

Peroni et al. (1997) "Flow Cytometric Analysis of Activation Markers on Stimulated T Cells and Their Correlation With Cell Proliferation", *Cytometry* 27:71–6.

Redd et al. (1992) "Allogeneic tumor–specific cytotoxic T lymphocytes", *Cancer Immunol. Immunother.* 34:349.

Rollino et al. (1995) "False positive results with MTT assay", *J. Immunol. Methods* 185:141–143.

Rosenberg et al. (1990) Gene transfer into humans–immunotherapy of patients with advanced melanoma, using tumor–infiltrating lymphocytes modified by retroviral gene.

Sastre–Garau et al. (1992) "Localisation ultrastructurale par immunocytochimie de la nucleoside diphosphate kinase/Nm23 dans des cellules carcinomateuses humaines", *Bull.*

Schirrmacher et al. (1995) "Workshop: active specific immunotherapy with tumor cells vaccines", *J. cancer Res. Clin. Oncol.* 121:487–489.

Slawson et al. (1993) "Are Papanicolaou Smears Enough? Acetic Acid Washes of the Cervix as Adjunctive Therapy: A HARNET Study?" *J. Fam. Pract.* 35:271–277.

Slawson et al. (1993) "Follow–up Pananicolaou Smear for Cervical Atypia: Are We Missing Significant Disease?" *J. Fam. Pract.* 36:289–293.

Sugata et al. (1991) "Rapid Counting Method of Living Cells by Fluorescent Enzyme Substrates", *Biomed Mater. Eng.* 1:115.

Taher et al. (1996) "Signaling Through CD44 Is Mediated by Tyrosine Kinases" *J. Biol. Chem.* 271:2863–7.

Tortora et al. (1997) "The $Rl_\alpha$ subunit of protein kinase A (PKA) binds to Grb2 and allows PKA interaction with the activated EGF–Receptor", *Oncogene* 14:923–8.

Tsou et al. (1983) "Evaluation of a One–Parameter Flow Analysis of Cervical Samples for Gynecology Cancer Screening" *Gynecol. Oncol.* 15, 316–324.

Volodin (1986) "Nonspecific gamma–esterase in the tissues in endometrial cancer", *Eksp. Onkol.* 8:49–52.

Watanabe (1975) "Aryl Hydrocarbon Hydroxylase in Morris Hepatoma 5123D", *Gann* 66:499–503.

Wood (1978) "Macrophages in Giant Cell Tumors of Bone", *J. Pathol.* 125:53–8.

Woytowicz et al. (1983) "Expression of Multiple Isozymes of Granulocyte, Monocyte, and Macrophage Esterases in Polycythemic Friend Erythroleukemia Cells", *Blood* 62:425–32.

Zarling et al. (1978) "Generation of cytotoxic T lymphocytes to autologous human leukaemia cells by sensitasation to pooled allogeneic normal cells", *Nature* 274:269–271.

Zubrikhina et al. (1990) "Use of automatic blood analyzer, Hemlog D, in cancer patients during radiotherapy and chemotherapy", *Vopr. Onkol* 36:81–85.

* cited by examiner

MEASURING ESTERASE ACTIVITY USING FLUORESCENT SUBSTRATES AS A WAY OF EVALUATING CERVICAL CANCER

This application is a continuation of PCT application Ser. No. PCT/US/15401, filed Jul. 8, 1999, which International Application was published by the International Bureau in English on Oct. 20, 2000, which application claims priority to U.S. application Ser. No. 60/092,210, filed on Jul. 8, 1998.

ACKNOWLEDGMENT OF GOVERNMENT SUPPORT

Not applicable.

FIELD OF INVENTION

This invention relates to methods of identifying cancerous cells and activated lymphocytes using fluorescent reagents. More specifically, it relates to the use of fluorescent reagents to identify and quantify cancerous cells and activated T and B cells. In some embodiments of the invention, the fluorescence assay is used in conjunction with a test to measure ploidy or marker expression of the cells.

BACKGROUND OF THE INVENTION

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site and/or metastases. Even in cancers such as breast cancer where the mortality rate has decreased, successful intervention relies on early detection of the cancerous cells. The etiology, diagnosis and ablation of cancer remain a central focus for medical research and development.

Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated. Early detection can help by allowing treatment in the early stages of the disease.

The three major cancers, in terms of morbidity and mortality, are colon, breast and lung. New surgical procedures offer an increased survival rate for colon cancer. Improved screening methods increase the detection of breast cancer, allowing earlier, less aggressive therapy. Numerous studies have shown that early detection increases survival and treatment options.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million. About half the number of people who develop cancer die of it.

Melanoma is one of the human diseases for which there is an acute need of new therapeutic modalities. It is a particularly aggressive form of skin cancer, and occurs in increased frequency in individuals with regular unguarded sun exposure. In the early disease phases, melanoma is characterized by proliferation at the dermal-epidermal junction, which soon invades adjacent tissue and metastasizes widely. Once it has metastasized, it is often impossible to extirpate and is consequently fatal. Worldwide, 70,000 patients are diagnosed with melanoma and it is responsible for 25,000 reported deaths each year. The American Cancer Society projects that by the year 2000, 1 out of every 75 Americans will be diagnosed with melanoma.

Neuroblastoma is a highly malignant tumor occurring during infancy and early childhood. Except for Wilm's tumor, it is the most common retroperitoneal tumor in children. This tumor metastasizes early, with widespread involvement of lymph nodes, liver, bone, lung, and marrow. While the primary tumor is resolvable by resection, the recurrence rate is high.

An estimated 178,000 new cases of lung cancer were diagnosed in 1997, accounting for 13% of cancer diagnoses. An estimated 160,000 deaths due to lung cancer occurred in 1997, accounting for 29% of all cancer deaths. The one year survival rates for lung cancer have increased from 32% in 1973 to 41% in 1993, largely due to improvements in surgical techniques. The 5 year survival rate for all stages combined is only 14%. The survival rate is 48% for cases detected when the disease is still localized, but only 15% of lung cancers are discovered that early.

Small cell lung cancer is the most malignant and fastest growing form of lung cancer and accounts for 20–25% of new cases of lung cancer. Approximately 60,000 cases were diagnosed in the U.S. in 1996. The primary tumor is generally responsive to chemotherapy, but is followed by wide-spread metastasis. The median survival time at diagnosis is approximately 1 year, with a 5 year survival rate of 5–10%.

Breast cancer is one of the most common cancers and is the third leading cause of death from cancers in the United States, with an annual incidence of about 180,200 new cases among women in the United States during 1997. About 1,400 new cases of breast cancer were diagnosed in men in 1997. In industrialized nations, approximately one in eight women can expect to develop breast cancer. The overall mortality rate for breast cancer has remained unchanged since 1930. It has increased an average of 0.2% per year, but decreased in women under 65 years of age by an average of 0.3% per year. Preliminary data suggest that breast cancer mortality may be beginning to decrease, probably as a result of increased diagnoses of localized cancer and carcinoma in situ. See e.g., Marchant (1994) Contemporary Management of Breast Disease II: Breast Cancer, in: *Obstetrics and Gynecology Clinics of North America* 21:555–560; and Colditz (1993) *Cancer Suppl.* 71: 1480–1489. Approximately 44,000 deaths (44,000 women, 300 men) in 1997 occurred due to breast cancer. In women, it is the second major cause of cancer death after lung cancer. The five-year survival rate for localized breast cancer has increased from 72% in the 1940s to 97% today. If the cancer has spread regionally, however, the rate is 76%, and for women with distant metastases the rate is 20%. Survival after a diagnosis of breast cancer continues to decline beyond five years. Sixty-five percent of women diagnosed with breast cancer survive 10 years and 56% survive 15 years.

Non-Hodgkin's B cell lymphomas are cancers of the immune system that afflicted approximately 225,000 patients in the United States in 1996. These cancers are diverse with respect to prognosis and treatment, and are generally classified into one of three grades. The median survival of the lowest grade is 6.6 years and the higher grade cancers have much lower life expectancy. Virtually all non-Hodgkin's B cell lymphomas are incurable. New diagnoses of non-Hodgkins lymphomas have increased approximately 7% annually over the past decade, with approximately 53,000 new diagnoses in 1996. The increase is due in part to the increasing prevalence of lymphomas in the AIDS patient population.

Colon and rectal cancer accounted for an estimated 131,000 cases in 1997, including 94,000 of colon cancer and 37,000 of rectal cancer. Colorectal cancers account for about 9% of new cancer diagnoses. About 55,000 deaths due to colorectal cancer occurred in 1997, accounting for about 10% of cancer deaths. Mortality rates for colorectal cancer have fallen 32% for women and 14% for men during the past 20 years, reflecting decreasing incidence rates and increasing survival rates. However, the mortality rate in African American men continues to rise. The 1 and 5 year relative survival rates for patients with colon and rectal cancer are 82% and 61%, respectively. When colorectal cancers are detected in an early, localized stage, the 5 year survival rate is 91%; however, only 37% of colorectal cancers are discovered at that stage. After the cancer has spread regionally to involve adjacent organs or lymph nodes, the rate drops to 63%. Survival rates for persons with distant metastases is 7%. Survival continues to decline beyond 5 years, and 50% survive 10 years.

In spite of the difficulties, effective cures using anticancer drugs (alone or in combination with other treatments) have been devised for some formerly highly lethal cancers. Most notable among these are Hodgkin's lymphoma, testicular cancer, choriocarcinoma, and some leukemias and other cancers of childhood. For several of the more common cancers, such as cervical cancer, early diagnosis, appropriate surgery or local radiotherapy enables a large proportion of patients to recover.

Cervical cancer is a relatively common, potentially lethal disease. This cancer produces few symptoms, except for irregular bleeding (usually postcoital). Cervical dysplasia most often affects women in their 20's; carcinoma in situ affects women 30 to 39 years of age; and invasive carcinoma affects women older than 40 years old. Klemm et al. (1996) *J. Obstet. Gynecol. Neonatal. Nurs.* 25:629–34. Advanced lesions require surgery and possibly radiation and chemotherapy. Guzinski (1987) *McGraw-Hill Encyclopedia of Science and Technology*, 6th Edition, Vol. 15, p. 359. An estimated 13,500 cases of invasive cervical cancer and 6,000 related deaths occur each year in the United States, with 160,000 related deaths occurring annually worldwide. Miller et al. (1992) *Am. Fam. Phys.* 45:143–150; and Burger et al. (1996) *J. Natl. Cancer Inst.* 88:1361–8.

The standard test for cervical cancer is the Papanicolaou technique, commonly known as a Pap smear. G. N. Papanicolaou, the father of exfoliative cytology, while examining vaginal smears for cytological changes related to the menstrual cycle, discovered the presence of highly abnormal cells which proved to be malignant tumor cells. He and H. F. Traut published their first studies in 1943 on the potential of cancer diagnosis from the examination of smears of the vaginal fluid. Since the cells accumulate in the body fluids by spontaneous shedding from adjacent organs, the procedure is generally referred to as exfoliative cytology. This type of examination is applied to practically every body fluid and frequently the cellular material is enriched by mechanical abrasion such as curettage or washing. This was an extremely important step in preventative medicine; the procedure is still in use primarily as a screening test in women for the detection of early uterine cancer. Barry (1987) *McGraw-Hill Encyclopedia of Science and Technology*, 6th Edition, Vol. 4, p. 36. It has been said that no other test has been as successful as the Pap smear in preventing cancer. DeMay (1997) *Arch. Pathol. Lab. Med.* 121:229–38.

However, there are several limitations to Pap smears. Because Pap smears involve the manual histologic examination of stained cellular smears, the technology is laborious and fraught with variation in interpretation leading to the potential for false negative diagnoses. Davey (1997) *Arch. Pathol. Lab. Med.* 121:267–9; Mitchell et al. (1995) *Cytopath* 6:368–75. Other problems with the Pap smear test include severe cytotechnologist shortages, lack of internal quality controls, and problems with classification of results. Slagel et al. (1995) *Diag Cytopath.* 13:26–30; and de Leon-Antoni (1991) *Bol. Asoc. Med. P. R.* 83:462–4. Furthermore, interpretation of cytologic findings is complicated by the fact that many different classification criteria are used for a single pathological condition. In addition, inflammatory change or hormonal evaluation are not included in the system and classification is not compatible with evaluation of endometrial lesions or chorionic disease. Kashimura et al. (1993) *Sangyo Ika Daigaku Zasshi* 15:37–43. Pap smears may also be unreliable in detecting cervical intraepithelial neoplasia (CIN). Slawson et al. (1993) *J. Fam. Pract.* 36:289–93. Due to questions about the reliability of the Pap smear, a follow-up smear or colposcopy, or acetic acid wash of the cervix is usually recommended after a positive result. Slawson et al. (1992) *J. Fam. Pract.* 35:271–7. False negatives, of course, are not subject to subsequent screening and can lead to unnecessary disease advancement.

The problems are thought to contribute to the high false positive report, which may be as great as 11.6%. Nenning et al. (1995) *Anal. Cell. Pathol.* 9:61–8; and Barry (1987) *McGraw-Hill Encyclopedia of Science and Technology*, 6th Edition, Vol. 4, p. 36. The rate of false-negatives has been subject to considerable debate, with most studies placing the rate between 5% and 28%. Naryshkin (1997) *Arch. Pathol. Lab. Med.* 121:270–272; Barry (1987) *McGraw-Hill Encyclopedia of Science and Technology*, 6th Edition, Vol. 4, p.36; and Lieu (1996) *J. Fam. Pract.* 42:391–9. However, at least one study places the false negative rate as high as 56%. Noel (1989) *J. Am. Board Fam. Pract.* 2:156–160. It is thought that no amount of training or experience with human observers can reduce the error rate to zero. Automated Pap screening holds the promise of higher sensitivity, but no instruments to date have been approved as a sole means of primary screening. Lieu (1996).

Once cancer is detected, any number of treatments can be used. Common treatments of cervical cancer, which are often applied to other cancers, include surgery, brachytherapy, external beam radiotherapy, chemotherapy, adjuvant therapy, and combinations of these therapies. Stockle et al. (1996) *J. Gynecol. Obstet. Biol. Reprod.* 25:244–52; Roy et al. (1996) *Gynecol. Oncol.* 62:336–339; Eifel (1997) *J. Surg. Oncol.* 66:141–7; Ngan et al. (1989) *Gynecol. Oncol.* 35:259–62; Curtin et al. (1997) *Surg. Oncol. Clin. N. Am.* 6:813–830; and Park et al. (1997) *Yonsei Med. J.* 38:255–60.

An emerging area of cancer treatment is immunotherapy. There are a number of immunological strategies under development, including: 1. Adoptive immunotherapy using stimulated autologous cells of various kinds; 2. Systemic transfer of allogeneic lymphocytes; 3. Vaccination at a distant site to generate a systemic tumor-specific immune response; and 4. Implantation of immune cells directly into the tumor.

Adoptive immunotherapy is directed towards providing the patient with a level of enhanced immunity by stimulating cells ex vivo (e.g., with a tumor-associated antigen or cytokine), and then re-administering them to the patient. The cells are histocompatible with the subject, and are generally obtained from a previous autologous donation. Zarling et al. (1978) Nature 274:269–71; U.S. Pat. Nos. 5,192,537; 5,308, 626; Rosenberg (1987) New Engl. J. Med. 316:889–897; Merchant et al. (1988) Cancer 62:665–671; Merchant et al. (1990) J. Neuro-Oncol. 8:173–198; and Rosenberg et al. (1990) New Engl. J. Med. 323:570–578.

In systematic (or adoptive) transfer of allogeneic lymphocytes, the goal is to create a general level of immune stimulation, thereby overcoming the anergy that prevents the host's immune system from rejecting the tumor. Strausser et al. (1981) J. Immunol. 127:266–271; Zarling et al. (1978) Nature 274:269–271; and Kondo et al. (1984) Med. Hypotheses 15:241–77.

The third immunotherapy strategy is the generation of an active systemic tumor-specific immune response of host origin. This is achieved by administering a vaccine composition at a site distant from the tumor. Various types of vaccines have been proposed, including isolated tumor-antigen vaccines and anti-idiotype vaccines. Another approach is to use tumor cells from the patient, or derivatives of such cells. Schirrmacher et al. (1995) J. Cancer Res. Clin. Oncol. 121:487–489; and U.S. Pat. No. 5,484,596. In yet another approach, autologous or syngeneic tumor cells are genetically altered to produce a costimulatory molecule. Pardoll et al. (1992) Curr. Opin. Immunol. 4:619–23; Saito et al. (1994) Cancer Res. 54:3516–3520; Vieweg et al. (1994) Cancer Res. 54:1760–1765; Gastl et al. (1992) Cancer Res. 52:6229–6236; and WO 96/07433. Tumor cells have been genetically altered to produce $TNF-_T$, IL-1, IL-2, IL-3, IL-4, IL-6, IL-7, IL-10, $IFN-_T$, $IFN-_K$ and GM-CSF.

The fourth immunotherapy strategy is intra-tumor implantation, which delivers effector cells directly to the tumor site. The proximity of the effector cells to the target is thought to promote the ability of the transplanted cells to react with the tumor, generating a graft versus tumor response. In studying adoptive immunotherapy of the 9L rat gliosarcoma cell line, Kruse et al. analyzed various effector cell populations, and found that tumor engraftment in the brain was prevented by allogeneic cytotoxic T lymphocytes prepared by coculturing thoracic duct lymphocytes from one inbred rat strain with spleen cells from rats syngeneic to the challenged animals. Kruse et al. (1990) Proc. Natl. Acad. Sci. USA 87:9377–9381; and Kruse et al. (1994) J. Neuro-Oncol. 19:161–168.

Redd et al. (1992) Cancer Immunol. Immunother. 34:349 describe a method of generating allogeneic tumor-specific cytotoxic T lymphocytes. CTL were generated in culture from an inbred rat strain allogeneic to the tumor cell line. The cells were found to lyse both tumor cells and Con A stimulated lymphoblasts of the same tissue type. The tumor-specific subset was deliberately selected and enriched as being specific for a determinant expressed only by the tumor.

More recently, Kruse et al. (Proc. Am. Assoc. Cancer Res. 36:474, 1995; FASEB J. 10:A1413, 1996) briefly outlined a clinical study of human brain cancer patients. The patient's lymphocytes were expanded with OKT3 and IL-2, then co-cultured with allogeneic donor cells for 18–21 days in the presence of IL-2. Such culture conditions would result in a population highly enriched for terminally differentiated effector cells.

Considerable progress was made towards a simpler and more effective immunotherapeutic strategy by the development of cytoimplants. WO 95/20649. Potent cellular compositions are placed directly into the tumor bed, leading to beneficial effects for patients with different types of cancers. The method can be conducted as follows: The tumor patient's leukocytes are co-cultured in a mixed lymphocyte cell reaction with healthy lymphocytes derived from an allogeneic donor. The alloactivated cells are surgically implanted at the tumor site, and produce a mixture of cytokines which induce a primary immune response. During this reaction, the host lymphoid cells identify both the graft lymphoid cells and tumor tissue as foreign.

In addition to the techniques referenced above, lymphocytes may be activated in vitro by contacting them with a variety of known lectins, mitogens, antigens (e.g. alloantigens), antibodies, other cells (as in MLC), or any combination of these stimulants. Cytotoxic T lymphocytes can be activated by, for example, immobilized anti-TcR monoclonal antibody, an immunocomplex of anti-TcR monoclonal antibody and immobilized rabbit anti-mouse antibody, a mixture of β-phorbol-12 myristate-13 acetate and ionophore A23187, and immobilized concanavalin A. U.S. Pat. No. 5,180,662. T cells can also be activated by superantigens (e.g. viral superantigens). Schafer et al. (1995) Adv. Pediatr. Infect. Dis. 10:369–90. Supplementing the growth medium with mouse serum rather than the conventional calf serum apparently enhances the mitogen-induced proliferation of human T lymphocytes. U.S. Pat. No. 4,596, 774.

Early activation events in T lymphocytes require the triggering of a tyrosine phosphorylation pathway involving one or more src family kinase. Weiss (1993) Cell 73:209–212. A limited number of these kinases, Lck, Fyn, and Yes, are expressed in T cells. Of these, the best-characterized is the lymphocyte-specific tyrosine kinase, P56 sup lck (Lck), whose unique N-terminal domain interacts with the cytoplasmic tails of the CD4 and CD8 glycoproteins. These glycoproteins bind to surface MHC class II and class I molecules, respectively, and participate with the T cell antigen receptor (TCR) in early events of T cell activation. Rudd et al. (1988) Proc. Natl. Acad. Sci. USA 85:5190–5194; Veillette et al. (1988) Cell 55:301–308; Shaw et al. (1989) Cell 59:627–636; Turner et al. (1990) Cell 60:755–765; and Shaw et al. (1990) Mol. Cell. Biol. 10:1853–1862.

Activated lymphocytes demonstrate altered expression of cellular markers. Known lymphocyte activation markers include CD25, CD30, CD38, CD44, CD45 (including isoforms CD45RA and CD45RO), CDw49b (VLA-2), CD56, CD69, CD71 (transferrin receptor), CD72, 4F2, HLA-DR, IL-2R (Interleukin-2 receptor), IRac, LFA-1 (lymphocyte activation marker), and serum neopterin. Norazmi et al. (1995) Immunol. Cell. Biol. 73:245–248; Chiba et al. (1995) J. Neurol. Sci. 132:170–173; Eskandari et al. (1997) Am. J. Physiol. 273:G727–34; Taher et al. (1996) J. Biol. Chem. 271:2863–7; Hughes et al. (1996) Am. J. Physiol 271:L79–84; Goodyear et al. (1996) Br. J. Dermatol. 134:85–93; O'Hanlon et al. (1996) Ann. Clin. Biochem. 33:536–9; Rabb et al. (1994) Am. J. Kidney Dis. 24:443–52; Carotti et al. (1994) Rheumatol. Int. 14:47–52; Engert et al. (1994) Leuk. Lymphoma 13:441–448; Yacyshyn et al. (1995) Int. J. Cancer 61:47–474; and Kawamura et al. (1991) Cell Immunol. 133:468–83. These markers demonstrate increased expression following lymphocyte activation. For example, LFA-1 levels increase after cells are induced with bacterial lipopolysaccharides, and serum soluble IL-2 receptor levels are higher in rheumatoid patients than in controls. Some of these markers have been studied for possible use in disease treatment. CD30, for example, is a target for immunotherapy of Hodgkin's lymphoma. Schnell et al. (1995) *Int. J. Cancer* 63:238–44; and Barth et al. (1996) *Ann. Oncol.* 7 suppl. 4:135–141.

Methods of determining lymphocyte activation would be useful in examination of the potency of any given antigen, antibody, or lectin. Thus, the potential of the immune cell as a therapeutic can be assessed prior to therapy. These methods may also be used to determine if a certain drug is capable of blocking lymphocyte activation, as demonstrated in, for example, U.S. Pat. No. 5,439,819.

Several methods have been devised for determining activation of lymphocytes. In the formazan reduction test, activated cells are treated with a tetrazolium compound, which the cell converts to formazan. The conversion is directly related to cell proliferation. Typical tetrazolium compounds used are 2,3-bis (2-methoxy-4-nitro-5-sulfophenyl)-2H-tetrazolium-5-carboxanilide (XTT) or 3-(4,5-dimethyl-2-thiazolyl)-2,5-diphenyl-2H-tetrazolium bromide (MTT). Another method of determining the extent of activation is determining the presence of surface receptors and surface immunoglobulins, such as those listed above. U.S. Pat. No. 4,402,934. These tests for lymphocyte activation are less than perfect; the positive predictive value of these tests may be as low as 60% to 70%. The tetrazolium tests are subject to a myriad problems. The MTT assay often generates false positive and false negative results. Rollino et al. (1995) *J. Immunol. Methods* 185:141–3; Nishida et al. (1992) *Hum. Cell* 5:87–98; Campos et al. (1974) *Arch. Intern. Med.* 133: 432–6; and Ashburn et al. (1973) *Blood* 41:9215. The tetrazolium assay may underestimate the cytotoxicity of toxic agents and does not reliably measure blood mononuclear cell responses. te Boekhorst et al. (1993) *Leukemia* 7:1637–44; and Chen et al. (1990) *Int. Arch. Allergy Appl. Immun.* 93:249–55. The MTT calorimetric assay is also relatively insensitive and unable to quantify fewer than 20,000 cells. Givens et al. (1990) *Invest. Opthalmol. Vis. Sci.* 31:1856–62. Tetrazolium also presents technical difficulties, in that the formazan dye crystals are largely insoluble. Monner (1988) *Immunol. Lett.* 19:261–8; and Kasugai et al. (1990) *Jpn. J. Pharmacol.* 52:95–100.

All references cited herein are hereby incorporated by reference in their entirety.

SUMMARY OF THE INVENTION

The present invention encompasses methods of determining whether a test cell is cancerous and also determining if a lymphocyte is activated based on measurements of the activity of an esterase or other enzyme and comparison with the activity in cancerous or activated cells respectively.

Accordingly, one embodiment of the present invention is a method of determining if a cell in a biological sample is cancerous by providing a biological sample comprising at least one mammalian test cell; measuring the activity or level of a protein in the test cell, where the activity or level of the protein in a cancerous cell is altered from that in a non-cancerous cell; and comparing the activity or level of protein in the test cell to the level or activity of the protein in a non-cancerous cell, where the activity or level of the protein in the test cell altered from that in a non-cancerous cell indicates a probability that the test cell is cancerous.

Another embodiment of the present invention is a method of determining whether a cell in a biological sample is cancerous by providing a biological sample comprising at least one mammalian test cell; measuring the esterase activity of the cell; comparing the esterase activity of the cell to the esterase activity of a non-cancerous cell, where the esterase activity of the test cell elevated over the esterase activity of the non-cancerous cell indicates a probability that the test cell is cancerous.

In another embodiment of the invention, the determination of the level of esterase activity is performed by adding to said sample a first reagent comprising a composition which, when cleaved by said esterase, produces a first product capable of producing a detectable signal; and detecting and measuring the level of said signal, where said level is indicative of the level of esterase activity in the cell.

In another embodiment of the invention, the method further comprises a measurement of the ploidy of the test cell in a method by determining the DNA ploidy of the cell; and comparing the ploidy of the cell to the ploidy of a non-cancerous cell, where the ploidy of the test cell greater than the ploidy of a non-cancerous cell indicates a probability that the test cell is cancerous. The point at which ploidy is determined in the test is irrelevant.

In another embodiment of the invention, the determination of ploidy is performed by adding to the sample a second reagent capable of interacting with the chromosomal DNA and producing a detectable signal; and detecting and measuring the level of fluorescence, where the signal level is correlated to the ploidy of the cell.

The test cell can be an animal cell, preferably a human cell. The human cell includes, but is not limited to, those derived from cervical, brain, lung, liver, stomach, prostate, breast, epithelial, blood, bone, bladder, or colon sources. The biological sample can also be obtained from a cervical swab smear, or biopsy, blood or tissue sample.

The first reagent preferably comprises a composition which, when cleaved by said esterase, fluoresces. Suitable fluorescent compositions include, but are not limited to, fluorescein or a derivative of fluorescein. The derivative of fluorescein includes, but is not limited to, fluorescein diacetate, carboxyfluorescein diacetate, halogenated fluorescein diacetate, carboxylated halogenated fluorescein diacetate, sulfofluorescein diacetate, azidofluorescein diacetate, fluoroscein monoacetate, carboxyfluorescein monoacetate, halogenated fluorescein monoacetate, carboxylated halogenated fluorescein monoacetate, sulfofluorescein monoacetate, azidofluorescein monoacetate, fluorescein conjugated to a sugar, fluorescein phosphate, fluorescein isothiocyanate, fluorescein isothiocyanate diacetate, carboxylated fluorescein, halogenated fluorescein and carboxylated, halogenated fluorescein, sulfofluorescein, and azidofluorescein.

Preferably, the carboxyfluorescein includes, but is not limited to, fluorescein diester, 5-carboxyfluorescein diacetate, and 6-carboxyfluorescein diacetate.

More preferably, the carboxylated halogenated fluorescein diacetate includes, but is not limited to, dichlorofluorescein diacetate and 6-carboxy-2',7'-dichlorofluorescein diacetate, and diacetyl-2,7-dichlorofluorescein.

The derivative of fluorescein includes, but is not limited to, fluorescein-di-θ-D-galactopyranoside, and fluorescein digalactoside.

In another embodiment of the invention, the second reagent is a DNA intercalating agent. Preferably, the DNA intercalating agent is ethidium bromide or propidium iodine.

Another embodiment of the invention is a method of determining if a cell in a biological sample is cancerous by providing a biological sample comprising at least one mammalian test cell; measuring the esterase activity in the cell by adding to the sample a compound which, when cleaved by the esterase, fluoresces; and detecting and measuring the fluorescence; comparing the esterase activity of the cell to the esterase activity of a non-cancerous cell, where esterase activity of the test cell elevated over the esterase activity of the non-cancerous cells indicates a probability that the test cell is cancerous.

In another embodiment of the invention, the measurement of the ploidy of the test cell by measuring the ploidy of the cell by adding to said sample a second reagent capable of interacting with the chromosomal DNA and fluorescing; detecting and measuring the level of fluorescence, where the level of fluorescence is correlated to the ploidy of the cell; and comparing the ploidy of the cell to the ploidy of a non-cancerous cell, where a ploidy of the test cell greater than the ploidy of a non-cancerous cell indicates a probability that the test cell is cancerous. Detection of ploidy and esterase activity can be performed in any order.

Another embodiment of the invention is a method of measuring activation of a lymphocyte by providing a test lymphocyte susceptible to activation by a stimulant; contacting the test cell with the stimulant under conditions suitable for lymphocyte activation; measuring the esterase activity of the test cell at least three days after performing step (b); and comparing the esterase activity of the test cell to the esterase activity of a cell which has not been activated, where esterase activity of the test cell altered from the esterase activity of a cell which has not been activated indicates a probability that the test cell has been activated.

Another embodiment of the invention is a method of measuring activation of a lymphocyte, wherein the determination of the level of esterase activity by adding to said sample a first reagent comprising a composition which, when cleaved by said esterase, produces a first product capable of producing a detectable signal; and detecting and measuring the level of said signal, where said level is indicative of the level of esterase activity in the cell.

In another embodiment, the cleavage of a fluorescein derivative is correlated with activation of the lymphocyte.

In another embodiment, the fluorescein derivative is fluorescein diacetate.

Another embodiment of the invention is a method of measuring activation of a lymphocyte, wherein the determination of activation of the test cell is further confirmed by measuring the reduction by the cell of a test compound, wherein said reduction is positively correlated to activation; and measuring the expression of an antigen, wherein expression of the antigen is positively correlated to activation.

In another embodiment, the test compound is a tetrazolium. Preferably the tetrazolium includes, but is not limited to, 2,3-bis(2-methoxy-4-nitro-5-sulfo-phenyl)-2H-tetrazolium-5-carboxanilide (XTT) or 3-(4,5-dimethyl-2-thiazolyl)-2,5-diphenyl-2H-tetrazolium bromide (MTT).

In another embodiment, the antigen is selected from CD69, CD25, CD69, CD71, and 4F2. Preferably the antigen is CD69.

In another embodiment, expression of the antigen is measured by an immunoassay or quantification of mRNA production.

In another embodiment, activation is mediated by at least another stimulant selected from lectins, mitogens, antigens, antibodies, or other cells.

DETAILED DESCRIPTION OF THE INVENTION

It would be highly advantageous to perform a method of screening for cancer cells and activated lymphocytes which is not as laborious and subject to variation in interpretation. Such a method would preferably allow high speed, automated screening of biological samples for the presence of cancer cells or activated lymphocytes. This would virtually eliminate the false positive and negative results inherent in manual screening procedures.

The present invention encompasses methods of determining whether a test cell is cancerous based on measurements of ploidy and/or the activity of an enzyme, where the level of enzyme activity is altered in a cancerous cell compared to a non-cancerous cell. The present invention also encompasses methods of determining if a lymphocyte is activated or not.

By "enzyme" is meant any protein with catalytic activity, including binding and/or cleaving or modifying a substrate. Preferably the enzyme has an altered activity level in cancerous cells. Enzymes known to have altered levels of activity in cancerous cells include, but are not limited to:

11q13 locus. Brison (1993) *Biochim. Biophys. Acta* 1155:25–41.

2–5A synthetase. Merritt et al. (1985) *Prog. Clin. Biol. Res.* 202:423–30.

Alpha-fetoprotein (AFP). Iwasaki et al. (1997) *Jpn. J. Clin. Oncol.* 27:278–81; Hyodo et al. (1996) *J. Gastroenterol.* 31:851–4; Shirabe et al. (1997) *J. Surg. Oncol.* 64:143–6; and Kanai et al. (1997) *Cancer Res.* 57:461–5.

L-arginine:NO pathway. Yim et al. (1996) *Korean J. Intern. Med.* 11:93–100.

Aryl hydrocarbon hydroxylase. Watanabe (1975) *Gann* 66:499–503.

Autocrine transforming growth factor. Reiss et al (1991) *Cancer Res.* 51:6254–62.

Calpactin I (annexin II) light chain. Wildrick et al. (1992) *Anticancer Res.* 12:1721–4.

Carbamoyl phosphate synthetase (glutamine-hydrolyzing). Aoki et al. (1981) *Science* 212:463–5.

Carcinoembryonic antigen (CEA). Hamori et al. (1997) *Acta Chir. Hung.* 36L125–7; Zaleska et al. (1997) *Rocz. Akad. Med. Bialymst.* 42 (suppl. 1): 179–89; and Alters et al. (1997) *Adv. Exp. Med. Biol.* 417:519–24.

Cathespin D (cathD). Escot et al. (1996) *Breast Cancer Res. Treat.* 38:217–26; and Vigneswaran et al. (1994) *Pathol. Res. Pract.* 190:1174–84.

CMP-NeuAc:Gal beta 1, 4G1cNAc-R alpha 2,6 sialyltransferase. Dall'Olio et al. (1989) *Int. J. Cancer* 44:434–9.

C-fos. Iwakura et al. (1995) *Virus Genes* 9:161–70.

C-jun. Iwakura et al. (1995) *Virus Genes* 9:161–70.

Cyclin D1. Gansauge et al. (1997) *Cancer Res.* 57:1634–7; and Zwijsen et al. (1996) *Mol. Cell. Biol.* 16:2554–60.

C-erbB-2/neu oncogene (p185HER2/neu). Byrne et al. (1995) *Cancer Res.* 55:2896–903; van de Vivjver et al. (1987) *Mol. Cell. Biol.* 7:2019–23; Pupa et al. (1993) *Oncogene* 8:2917–23; Sauter et al. (1993) *Cancer Res.*

53:2199–203; Meden et al. (1994) *J. Cancer Res. Clin. Oncol.* 120:378–81; Andersen et al. (1995) *Acta Oncol.* 34:499–504; Schneider et al. (1996) *Anticancer Res.* 16:1197–202; Felip et al. (1995) *Cancer* 75:2147–52; D'souza et al. (1994) *Proc. Natl. Acad Sci. USA* 91:7202–6; and Meden et al. (1994) *J. Cancer Res. Clin. Oncol.* 120:378–81.

D52m. Byrne et al. (1995) *Cancer Res.* 55:2896–903.

Elongation factor 1γ (EF1γ). Mimori et al. (1996) *Gut* 38:66–70.

Epidermal growth factor receptor (EGFR)/EGF/ transforming growth factor α (TGF-α). Yamanaka et al. (1993) *Anticancer Res.* 13:565–9.

Esterases. Described in detail below.

Heparin-binding growth factor type 2/basic fibroblast growth factor (HBGF-1/bFGF). Sternfeld et al. (1988) *J. Cell. Physiol* 136:297–304.

Hepatocyte growth factor/scatter factor. Olivero et al. (1996) *Br. J. Cancer* 74:1862–8; and Joseph et al. (1995) *J. Natl. Cancer Inst.* 87:372–7.

HOX2 homeobox gene. Simeone et al. (1990) *Nature* 346:763–6; and Faiella et al. (1994) *Proc. Natl. Acad. Sci. USA* 91:5335–9.

Inosine 5'-monophosphate dehydrogenase (IMP DH). Weber et al. (1991) *Cancer Commun.* 3:61–6.

Insulin-like growth factor II (IGF2). Zhan et al. (1994) *J. Clin. Invest.* 94:445–8.

Int-1 proto-oncogene. Meden et al. (1994) *J. Cancer Res. Clin. Oncol.* 120:378–81; and Shackleford et al. (1987) *Cell* 50:89–95.

Melanoma antigen-encoding gene-1 (MAGE-1). Katano et al. (1997) *J. Surg. Oncol.* 64:195–201.

Mitogen-activated protein (MAP) kinases. Li et al. (1994) *Oncogene* 9:647–9.

Multi-drug resistance (P-glycoprotein) mdr1a and mdr3. Teeter et al. (1993) *Mol. Carcinog.* 8:67–73; and Teeter et al. (1993) *Mol. Carcinog* 8:67–73.

MSX-2. Takahashi et al. (1996) *Oncogene* 12:2137–46.

MUC1. Vos et al. (1991) *Biochem. Biophys. Res. Commun* 181:121–30.

MUC5. Yu et al. (1996) *Int. J. Cancer* 69:457–65.

Myc, c-myc. Brison (1993) *Biochim. Biophys. Acta* 1155:25–41.

Neu oncogenes. Sukumar et al. (1990) *Proc. Natl. Acad. Sci USA* 87:718–22.

NSE. Zaleska et al. (1997) *Rocz. Akad. Med. Bialymst.* 42 (suppl. 1):179–82.

Nucleoside diphosphate (NDP) kinase/nm23. Sastre-Garau et al. (1992) *Bull. Cancer* 79:465–70.

P815AB tumor antigen encoded by P1A. Uyttenhove et al. (1997) *Int. J. Cancer* 70:349–56.

P53. Lacombe et al. (1996) *J. Clin. Oncol.* 14:2646–52; and Freedman et al. (1996) *Br. J. Cancer* 73:902–8.

Parathyroid hormone-related peptide (PTHrP). Sidler et al. (1996) *J. Clin. Endocrinol. Metab.* 81:2841–7.

Peroxidase. Zubrikhina et al. (1990) *Vopr. Onkol.* 36:81–85.

Protein kinase A (PKA). Tortora et al. (1997) *Oncogene* 14:923–8.

Protein kinase C (PKC). La Porta et al. (1997) *Carcinogenesis* 18:715–9.

Cyclic AMP-dependent protein kinase. Malkinson et al. (1977) *Biochem. J.* 168:319–321.

Pyrimidine nucleoside phosphorylase (PyNPase). Kirita et al. (1995) *Gan To Kagaku Ryoho* 22:509–14.

Ras, K-ras, H-ras, N-ras oncogenes. Brison (1993) *Biochim. Biophys. Acta* 1155:25–41; Finkel et al. (1984) *Cell* 37:151–8; Stanley (1995) *Toxicology* 96:173–94; Janssen et al. (1985) *Cancer Res.* 45:3262–7; Burns et al. (1991) *J. Radiat. Res.* 32:202–16; and Jamal et al. (1994) *Oncogene* 9:417–23.

T-cell receptor (TCR) repertoire, including V beta 2. Valteau et al. (1996) *Cancer Res.* 56:362–9.

Telomerase. (1995) *JNCI* 12:1–2.

Tenascins. Chiquet-Ehrismann (1995) *Experientia* 51:853–62.

Thymidylate synthase. Speth et al. (1988) *Clin. Pharm. Ther.* 44:369–75.

Tissue inhibitor of metalloproteinases (TIMP).

Vascular endothelial growth factor. White et al. (1995) *Growth Factors* 12:289–301.

Xmrk receptor tyrosine kinase. Malitschek et al. (1994) *J. Biol. Chem.* 269:10423–30.

Most preferably, the enzyme whose change in activity is detected by the method of the present invention is an esterase. Preferably, the esterase is capable of cleaving a reagent, and more preferably, the esterase cleaves a fluorescein derivative to produce a fluorescent product. Esterases include, but are not limited to, nonspecific esterases, alpha-esterase, β-K-esterase, naphthol chloracetate esterase (NCAE); guanidinobenzoate esterase; alpha naphthyl acetate esterase (ANAE); and other esterases. A positive naphthol AS-D chloroacetate esterase stain in granulocytic sarcoma is a differential diagnosis between malignant lymphoma and granulocytic sarcoma. Spahr et al. (1982) *Acta Cytol.* 26:55–60.

Non-specific esterases commonly demonstrate an increase in activity in cancerous tissues. An increase in the production of nonspecific tissue Kesterase (NTE) accompanies formation of endometrial malignancies. NTE content in uterine tissues and mucus of patients with cancer of endometrium correlates with a degree of differentiation, spreading and depth of tumor cell invasion into the myometrium. Volodin (1986) *Eksp. Onkol.* 8:49–52. Non-specific esterase activity was also demonstrated in tumor cells from tumor located in the anterior mediastinum. Oosterhuis et al. (1991) *Cancer Genet. Cytogenet.* 54:183–95. Elevated levels of non-specific esterase were also found in leukocytes in patients with severe leukopenia. Zubrikhina et al. (1990) *Vopr. Onkol.* 36:81–85. The amounts of fluoride-sensitive and -resistant nonspecific esterase activity increased with the progression of malignancy of erythroleukemic cells. Woytowicz et al. (1983) *Blood* 62:425–32. Significant nonspecific esterase positivity was also observed in bone tumor sections. Wood (1978) *J. Pathol.* 125:53–8.

High esterase levels are associated with urological tumor cells which continued to proliferate after treatment with chemotherapeutic agents; cells which were inhibited demonstrated low esterase activities. Flanigan et al. (1986) *J. Urol.* 135:1091–100; and Pavlik et al. (1985) *Cancer Invest.* 3:413–26. Naphtholesterases demonstrated strong enzyme activity in lobules of invasive carcinoma, and were correlated with a high degree of differentiation of the tumor. This finding offered an interesting contribution for the fine evaluation of histoprognosis in malignant epithelial tumors. Chomette et al. (1984) *Pathol. Biol.* 32:995–1003. A positive naphthol AS-D chloroacetate esterase stain in granulocytic sarcoma may be used as a differential diagnosis between malignant lymphoma and granulocytic sarcoma. Spahr et al.

(1982) *Acta Cytol.* 26:55–60. In solid Ehrlich ascite tumor cells, the activity of naphthol-AS-acetate esterase was significantly higher than in other cells. Bauer et al. (1977) *Arch. Geschwulstforsch* 47:236–40. Urinary alpha-esterase levels were elevated in bilharzial bladder cancer patients compared to normal controls. el-Sewedy et al. (1978) *Trans. R. Soc. Trop. Med. Hyg.* 72:525–8. Depressed levels of C1 esterase inhibitor is manifested in hereditary angioedema. Brasher et al. (1975) *Arch. Dermatol.* 111:1140–42.

In the case of other esterases, esterase levels may be reduced in cancerous cells, compared to normal cells of the same type. For example, alpha naphthyl acetate esterase (ANAE) activity was lower in liver, colon and breast tumor cells than in non-tumoric surrounding tissues. Lund-Pero et al. (1994) *Anticancer Res.* 14:2747–53. A decrease in levels of esterase D, an enzyme mapping to 13q14.11, is associated with loss of one chromosome 13, and a null allele of esterase D is a marker for genetic events in retinoblastoma formation. Lee et al. (1987) *Hum. Genet.* 76:33–36; and Benedict et al. (1983) *Science* 219:973–5. N-acetyl arginine esterase activity may also be lower in malignant mucosa cells. Paskhina et al. (1984) *Vopr. Med. Khim.* 30:87–96. In general, determination of esterase levels of a cancer cell are made in comparison to esterase levels in a normal cell of the same or a similar type of tissue.

Altered levels or activities of an esterase or any other protein may be determined by any of a number of techniques. For example, standard methods of molecular biology such as Western blots can be used to detect increased abundance of a protein product; Northern blots can be performed to detect increases in levels of the corresponding mRNA. Antibodies to specific proteins can also be conjugated to fluorescent markers or enzymes that modify a substrate to produce a detectable signal, or conjugated to the signal-producing moiety itself. Such techniques are commonly known in the art and described, for example, in *Molecular Cloning: A Laboratory Manual,* 2nd ed., Vol. 1–3, eds. Sambrook et al. Cold Spring Harbor Laboratory Press (1989); and *Current Protocols in Molecular Biology,* eds. Ausubel et al., Greene Publishing and Wiley-Interscience: New York (1987) and periodic updates. In the case of enzymes (such as esterases) enzyme cleavage of a natural or artificial substrate can produce a detectable signal. For example, esterases cleave substrates such as fluorescein-derived compounds and thereby produce a fluorescent product. The level of fluorescence is correlated to the abundance of the esterase.

By "fluorescein-derived compound", "fluorescein derivative", and the like, is meant any compound which can be cleaved by an esterase to produce a fluorescent compound. By "a fluorescent compound" is meant a compound which fluoresces when exposed to an appropriate level and wavelength of light, as is well-known in the art. For example, when excited by blue light, fluorescein emits an intense yellow-green fluorescence. Preferably, this compound comprises fluorescein or a derivative of fluorescein. The derivatives of fluorescein include, but are not limited to, fluorescein diacetate, carboxyfluorescein diacetate, halogenated fluorescein diacetate, carboxylated halogenated fluorescein diacetate, sulfofluorescein diacetate, azidofluorescein diacetate, fluoroscein monoacetate, carboxyfluorescein monoacetate, halogenated fluorescein monoacetate, carboxylated halogenated fluorescein monoacetate, sulfofluorescein monoacetate, azidofluorescein monoacetate, a compound comprising fluorescein conjugated to a sugar, fluorescein phosphate, fluorescein isothiocyanate (FITC), fluorescein isothiocyanate diacetate, carboxylated fluorescein, halogenated fluorescein and carboxylated, halogenated fluorescein, sulfofluorescein, and azidofluorescein. Carboxyfluorescein include, but are not limited to, fluorescein diester, 5-carboxyfluorescein diacetate, and 6-carboxyfluorescein diacetate. Carboxylated halogenated fluorescein diacetates include, but are not limited to, 5-carboxy-2',7'-dichlorofluorescein diacetate and 6-carboxy-2',7,7'-dichlorofluorescein diacetate, and diacetyl-2,7-dichlorofluorescein. A fluorescein derivative include, but are not limited to, fluorescein-di-θ-D-galactopyranoside, and fluorescein digalactoside. Preferably, the fluorescein derivative is fluorescein diacetate or FITC.

It has now been found that determination of whether a test cell has an esterase level typical of a cancer cell can be made by first staining the test cell with a fluorescein derivative. The fluorescein derivative enters the cell, where it is cleaved by an esterase to produce a fluorescent product. The cell is then placed under conditions wherein the fluorescent product fluoresces (e.g., placed in a cell sorter and exposed to a light of a wavelength suitable for exciting the fluorescent product to produce a light signal). Cell sorters and automated detectors of fluorescence are known in the art. Herzenberg et al. (1976) *Sci. Am.* 234:108–116; Kamarck (1987) *Methods Enz.* 151:150–165; and Nolan et al. (1988) *Proc. Natl. Acad. Sci. USA* 85:2603–2607. Within the cell sorter, the signal is detected and quantified. Cells known to be cancerous and non-cancerous are treated in the same way to determine typical levels of fluorescence of the same product in these cells. Finally, a comparison is made between the fluorescence of the product in the test cell with that of the same product in cancer and non-cancerous cells. Typically, cancerous cells will have a higher fluorescence due to esterase activity altered from that of non-cancerous cells. In addition to altered enzymatic levels or activity, cancerous cells can also demonstrate an altered ploidy.

By "ploidy" is meant an indication of the number of sets of chromosomes within a cell. Monoploid indicates the basic or haploid number of chromosomes; diploid is twice this number. Euploidy also indicates a correct number of chromosomes (e.g., a diploid number). A cancer cell is "aneuploid" if it does not have the normal diploid number due to chromosome loss or an excess in chromosomes. "Hypoploidy" indicates loss of portions of or complete chromosomes. "Hyperploidy" or "hyperdiploidy" indicates that a cell contains more than the diploid number. Although standards vary, a chromosome number averaging at least 1.1 or 1.2 times the diploid number indicates hyperploidy or hyperdiploidy. These two latter terms partially overlap with the terms "tetraploidy" (twice the diploid number) and "hypertetraploidy" (more than twice the diploid number).

Aneuploidy has been used as both an indicator of the malignancy of tumors, and an indicator of possible outcome. Patients in which tumors demonstrate aneuploidy may have a significantly shorter survival rate than those with euploid tumors. Liewald et al. (1992) *Anal. Cell. Pathol.* 4:103–114; Kearseley et al. (1990) *Br. J. Cancer* 61:821–7; Esteban et al. (1991) *Am. J. Clin. Pathol.* 95:460–6; and Jones et al. (1990) *Cancer* 66:752–7.

Hyperploidy is correlated with high grade dysplasia of cervical-vaginal cytology smears. Kurtycz et al. (1996) *Diagn. Cytopathol.* 15:46–51. In addition, aneuploidy is correlated with a number of different types of cancer, including, but not limited to, lung carcinoma, lymphoblastic leukemia, and pancreatic, colonic, colorectal and urothelial cancer, and the correlation between malignancy and aneuploidy has been studied particularly thoroughly with breast cancer tumors. Liewald et al. (1990) *Cytometry* 11:341–8;

Taguchi et al. (1996) *J. Pediator Hematol. Oncol.* 18:113–21; Bychkova et al. (1996) *Vopr. Onkol.* 42:40–44; Planz et al. (1996) *Gen. Diagn. Pathol.* 142:69–73; Cohn et al. (1997) *Cancer* 79:233–44; Southern et al. (1996) *Cancer* 77:58–62; Bychkova et al. (1997) *Vopr. Onkol.* 43:171–5; Sato et al. (1997) *Cancer* 115:47–55; Shackney et al. (1995) *Cytometry* 22:282–91; Giaretti et al. (1996) *Am. J. Pathol.* 149:237–45; and Jarvinen et al. (1996) *Am. J. Pathol.* 148:2073–82.

Several methods are available to determine ploidy. These include fluorescence in situ hybridization (FISH) [Marshall et al. (1996) *Mutat. Res.* 372:233–45; and Hande et al. (1997) *Mutagenesis* 12:125–31]; flow cytometry (FCM) [Stonesifer et al. (1987) *Acta Cytol.* 31:125–30; Remvikos et al. (1988) *Int. J. Cancer* 42:539–43; and Bronner et al. (1988) *Am. J. Clin. Pathol.* 89:764–9]; the Schutte method and the Hedley method [Tagawa et al. (1993) *Cytometry* 14:541–9]; Magnetic Resonance (MRI) [Takashima et al. (1996) *Am. J. Roentgenol.* 167:1297–304]; the stemline interpretation technique [Borchers et al. (1994) *Urol. Int.* 52:145–150]; and the analysis of spindle apparatus anomalies [Kochendorfer et al. (1996) *Mutat. Res.* 361:55–66]. Normal cells or those otherwise known to be diploid are commonly used as controls.

By "intercalating agent" is meant any agent capable of binding to DNA to produce a fluorescent product. By "a fluorescent compound" is meant a compound which fluoresces when exposed to an appropriate level and wavelength of light, as is well-known in the art. For example, when excited by ultraviolet light, ethidium bromide produces a visible light signal. Preferably, the intercalating agent includes, but is not limited to, ethidium bromide, propidium iodide, or another large planar compound capable of inserting itself between the bases in DNA. Fluorescence is correlated with the amount of DNA in the cell and thus indicative of relative ploidy.

Ethidium bromide and other intercalating agents have been used to differentiate between living and dead cells, with the agents permeating the leaky cell membranes of dead cells, but not the intact cell membranes of living cells. In order to stain living cells for staining with ethidium bromide, cell membranes must be permeabilized. Preferably, this is done by exposing the cells for a short time with a low (non-toxic) level of a detergent. Suitable detergents include, but are not limited to, Triton X-100™ (polyoxyethylene-p-t-octylphenol) and Nonidet P-40™. Alternatively, cells in a solution of intercalating agent are micro-injected or exposed to a very short electrical shock (e.g., 2000 volts per centimeter for 200 microseconds), which causes transient pores to form in the plasma membrane without damaging intracellular membranes. The pores remain open for minutes or hours, depending on the cell type and degree of the electric shock, allowing entry of the intercalating agent. In an alternative method, membrane-bounded vesicles containing the intercalating agent can be induced to fuse with the plasma membrane of the cells. This allows entry of the intercalating agents into the cells. Vesicles can be formed by any technique known in the art, including, for example, mixing a concentrated solution of intercalating agent with a suspension of phospholipids and agitating the suspension ultrasonically to create liposomes. Alternately, red blood cells can be converted into loaded membrane-bound vesicles by bursting them to remove their natural contents and then allowing their plasma membranes to reseal while immersed in a solution of intercalating agent. Either the liposomes or red cell ghosts can be induced to fuse with the target cells by the presence of certain viral fusion-inducing proteins (produced by the viruses to help them get into the cells). Gomperts et al. (1985) *Trends Biochem. Sci.* 10:414–417; and Ostro (1987) *Sci. Am.* 256:102–111.

A determination of ploidy can be made by first staining the test cell with an intercalating agent. This agent enters the cell, where it interacts with the chromosomal DNA to produce a fluorescent product. The cell is then placed under conditions wherein the fluorescent product fluoresces (e.g., placed in a cell sorter and exposed to ultraviolet light). Within the cell sorter, the signal is detected and quantified. Cells known to be cancerous or non-cancerous are treated in the same way to determine typical ploidies of these cells. Finally, a comparison is made between the fluorescence of the fluorescent product in the test cell with that of the same product in the cancer and non-cancerous cells. Typically, cancerous cells will have a higher fluorescence due to higher ploidy than non-cancerous cells.

An indication that the test cell has an altered esterase activity and an altered ploidy compared to a non-cancerous cell indicates a probability that the test cell is a cancer cell.

The present invention also encompasses methods of using fluorescent reagents to detect activated lymphocytes.

"Activation," "stimulation," and similar terms are used to describe the biochemical change that occurs in order to increase the immunological potency of a lymphocyte. By "lymphocyte" is meant any immunological cell with a large nucleus and relatively thin layer of cytoplasm, including, but not limited to, T cells, B cells, monocytes, neutrophils, eosinophils, and basophils. Lymphocytes can be activated by external stimulation, e.g. culture in the presence of any stimulant, including but not limited to, a cytokine, lectin, antigen (including, but not limited to, allo-antigens and superantigens), antibody, or another cell (e.g. in a MLC). Mononuclear cells, for example, can be activated by culturing them ex vivo in the presence of tumor cell extract and a non-specific activator like phytohemagglutinin or IL-1. U.S. Pat. No. 5,192,537.

"Mixed lymphocyte reaction", "mixed lymphocyte culture", "MLR", and "MLC" are used interchangeably to refer to a mixture comprising a minimum of two allotypically different cell populations. At least one of the allotypically different cells is a lymphocyte. The cells are cultured together for a time and under suitable conditions to result in the stimulation of the lymphocytes. A frequent objective of MLC is to provide allogeneic stimulation to initiate proliferation of the lymphocytes; but unless indicated, proliferation during the culture is not required. In the proper context, these terms can alternatively refer to a mixture of cells derived from such a culture. When cells from MLC are administered as a bolus to a human, especially in a tumor bed, it is referred to as a "cytoimplant". Following administration of a cytoimplant, the therapeutic effect or immunologic response can be boosted by implanting in or around the bed of a solid tumor in the patient a second cell population comprising alloactivated human lymphocytes allogeneic to the patient. Multiple cytoimplants or combinations of implants and cellular vaccines could be given to the same patient, but some attention should be paid to the possibility that the allogeneic lymphocytes in the vaccine may generate an anti-allotype response. The use of a mixture of allogeneic cells from a plurality of donors, and the use of different allogeneic cell populations in each dose, are both strategies that can help minimize the occurrence of an anti-allotype response.

Modes of Carrying Out the Invention

In the method of the present invention, cells are tested to determine if they are normal or cancerous and lymphocytes are tested to determine if they are unactivated or activated. Such determinations are based on the findings, described above, that cancerous cells have altered protein or enzyme levels or activities. The protein or enzyme level or activity of the test cell is determined and compared to that of a non-cancerous cell. A cancerous cell can also be used as a control. In addition, the ploidy of the test cell can be determined and compared to that of a non-cancerous cell control. Altered enzyme levels or activity and altered ploidy indicate that the cell is cancerous.

In the present method, test cells are obtained through any technique known in the art, including, but not limited to, extraction of bodily fluids or mechanical abrasion such as curettage or washing. Preferably, for analysis of potentially cancerous cells from the cervix, Pap smear material is collected by standard techniques for analysis. In flow cytometric cancer detection, cells can be suspended in saline by agitation with the extraction instrument (e.g, brush or spatula) in a test tube containing the fluid.

Test cells are then exposed to a first reagent which tests the level or activity of a given protein or enzyme known to have an altered level or activity in a cancer cell. Preferably, the protein is an enzyme, and more preferably, an esterase. The first reagent can be, for example, an antibody, an antibody conjugated to a enzyme that cleaves a substrate to produce a detectable signal, or an antibody conjugated to a substrate cleaved by an enzyme to produce a detectable signal. As another example, the reagent can be a radiolabeled polynucleotide probe used to detect levels of the mRNA translated to produce the protein or enzyme. In addition, in the case of an enzyme, the first reagent is, preferably, a substrate which is cleaved by the enzyme to produce a detectable signal. More preferably, in the case of esterases, the reagent is a substrate cleaved to produce a fluorescent signal. Even more preferably, the reagent is a fluorescein-derivative. The use of antibodies, probes and fluorescent reagents is known in the art and exemplified in, for example, *Molecular Cloning: A Laboratory Manual,* 2nd ed., Vol. 1–3, eds. Sambrook et al. Cold Spring Harbor Laboratory Press (1989); and *Current Protocols in Molecular Biology,* eds. Ausubel et al., Greene Publishing and Wiley-Interscience: New York (1987) and periodic updates and references cited therein.

The level of the signal generated is then detected. In the case of an antibody conjugated to an enzyme which cleaves a substrate to produce a detectable signal, the substrate is then added to the cell and the signal detected. In the case of an antibody conjugated to a substrate which is cleaved to produce a detectable signal, the enzyme is then added to the cell and the signal detected. In the case of the use of a fluorescent reagent such as a fluorescein-derivative, the cells may be placed into a flow cytometer and the fluorescence detected, as is known in the art. Non-cancerous and cancerous cells may be treated in the same way and used as a control; a level of signal dissimilar to that of a non-cancerous cell and similar to that of a cancerous cell indicates that the test cell is cancerous.

In addition, before, after, or during the testing of the level of protein or enzyme level or activity, the test cell may be tested for ploidy. Several techniques are listed above for determining ploidy. Preferably, the cells are treated with a second reagent which binds to the chromosomes of the test cell and produces a fluorescent product. More preferably, the cells are treated with a detergent and an intercalating agent. More preferably, the intercalating agent is ethidium bromide or propidium iodide. The level of fluorescence of the cells can be determined by any method known in the art, including, preferably, passing the cells through a flow cytometer, which will measure the fluorescence of the cells and thereby determine the cell's ploidy. A determination that the cell has an altered ploidy (e.g. hyperdiploidy or hypoploidy) is an indication that the test cell is cancerous.

An indication that the test cell is aneuploidy and has an altered esterase level provides greater assurance that the cell is cancerous.

The following examples are provided to illustrate but not limit the present invention.

EXAMPLE 1

Preparation of Test Cells for Analysis

In accordance with the present invention, fluorescent reagents such as fluorescein diacetate are used to determine whether cells are cancerous and whether lymphocytes are activated. Optionally, another fluorescent agent such as an intercalating agent (e.g., ethidium bromide or propidium bromide) can also be used to determine ploidy, or a test can be performed to determine expression of cancer-specific markers.

Test cells can be obtained from a patient through any techniques known in the art, such as extraction of bodily fluids or mechanical abrasion such as curettage or washing. For analysis of test cells from the cervix, Pap smear material can be collected by standard techniques for analysis. Lymphocytes can be tested after exposure to antigens for activation.

In an exemplary test, test cells are suspended in phosphate-buffered saline (PBS). Then the cell suspension is stained for 30 minutes at room temperature by the addition of a final concentration of about 0.01 to about 0.1 $\mu$g/ml fluorescein diacetate (stock in DMSO). After a brief (10 to 20 min) fixation in 0.5% paraformaldehyde, cells are optionally further stained by the addition of 0.1 to 1 $\mu$g/ml ethidium bromide (or propidium iodide) and 0.05% Triton-X100™ detergent.

After staining, test cells are analyzed for their fluorescent properties using a fluorescence activated cell sorter (FACS) or fluorescence microscope. The level of fluorescence of the fluorescein compound and the intercalating agent, which are correlated to the relative levels of esterase activity and ploidy, are measured and recorded, preferably, automatically. These results are compared to control results obtained from cells known to be cancerous and/or normal or non-cancerous, or, in the case of lymphocytes, compared to cells known to activated or unactivated.

EXAMPLE 2

Analysis of Cancerous Cells Using Fluorescein Derivatives

Cancerous and non-cancerous tissues were used to verify the validity of the use of fluorescent compounds to determine if cells were cancerous.

Material from a hysterectomy specimen was obtained, stained and analyzed by flow cytometry as described above. The specimens came from a 64-year-old female with cervical squamous cell carcinoma. Samples were also taken from a normal cervix (A), a cervical carcinoma (B), and normal endometrium (C), by swabbing the specimen gently with a cotton swab.

Figure 1:
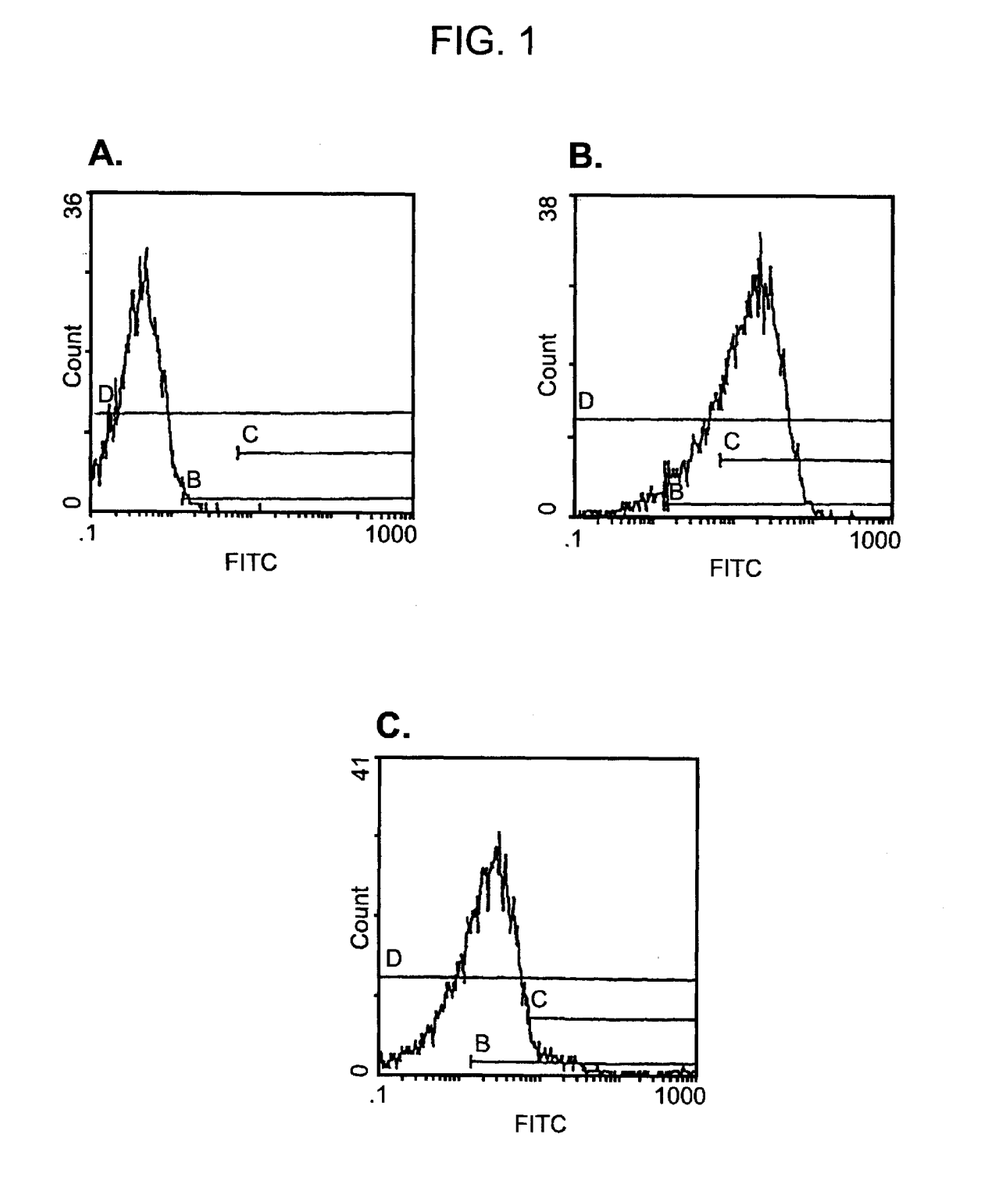
FIG. 1 depicts the pattern of fluorescence of a fluorescein derivative in normal cervical cells (A), cervical squamous carcinoma cells (B), and normal endometrial cells (C).

Cells were shaken loose from the swab in PBS, and then stained with fluorescein diacetate and ethidium bromide. The results, shown in FIG. 1, indicate that normal cervical cells and normal endometrial cells have a lower relative fluorescence than carcinoma cells. The normal cervical cells peaked at a relative fluorescence of about 0.4 to 0.5; normal endometrial cells peaked at around 2 to 3. In contrast, carcinoma cells peaked at around 20 to 30. Thus, in this example, cancerous cells demonstrated a fluorescence one or two orders of magnitude higher than that of non-cancerous cells. This same pattern has been repeated with specimens from other patients.

These data verified that cancerous cells demonstrate an altered fluorescence pattern than non-cancerous cells when treated with a fluorescent reagent.

EXAMPLE 3

Analysis of Cancerous Cells Using Fluorescein Derivatives

As in the previous example, a fluorescent reagent such as FDA (fluorescein diacetate) can be used to identify abnormal cells in a Pap smear material. After cells are labeled with FDA, flow cytometry can be used to identify abnormal cells. The experiments described below were performed using pathology material, usually from hysterectomy specimens. Various areas of each specimen were swabbed with cotton swabs, thereby collecting an assortment of cell populations, such as cells from ectocervix (outer cervical surface), endocervix (inner portion or cervix), or endometrium (mucus membrane lining uterus). Most cancers or areas of dysplasia occur in the endocervical region. Cells obtained from these various areas can be smeared on glass slides for microscopic analysis or used for flow cytometry. Examination of the cell smears confirms the presence of malignant or dysplastic cells, and this information can be used for proper interpretation of flow results. The following results were obtained from a number of cases. No attempt to standardize the staining between cases was made and direct comparison should be avoided.

For flow cytometry, cells were dislodged from the cotton swabs by vigorous mixing in 2 mL PBS. Cells were stained by mixing 0.2 mL of the cell suspension with 10 $\mu$L of freshly diluted FDA. A stock solution of 10 mg/mL of FDA in DMSO was diluted in PBS at 1:10 to 1:1000. Staining was halted by the addition of 0.5 mL of 0.5% paraformaldehyde in PBS. In most cases flow cytometry was performed within 4 hours. The mean values reported below represent the fluorescence mean of the population after counting 5000–10, 000 cells. In cases where malignant or dysplastic cells were confirmed, these cells were confined to the ectocervical specimen and the mean values for these specimens are in bold lettering. Data are presented in Table 1, where CIN stands for Cervical intraepithelial neoplasia. In an attempt to make the data more comparable, the ratio of mean values from the endocervix were divided by the ectocervical values.

In most cases, a endocervix/ectocervix ratio above about 4 correlates with malignancy. Thus, these data provide further evidence that fluorescent reagents can be used to determine whether cells are cancerous.

TABLE 1

| Experiment | Diagnosis | Site | Mean fluorescence | Ratio: Endocervix/ Ectocervix or Endometrium/ Ectocervix |
|---|---|---|---|---|
| Case #1 | CIN III | Ectocervix | 1.48 | NA |
| | | Endocervix | 5.13 | 3.47 |
| | | Endometrium | 2.81 | 1.89 |
| Case #2 | Squamous Cell Carcinoma | Ectocervix | 0.71 | NA |
| | | Endocervix | 17.7 | 24.89 |
| | | Endometrium | 4.41 | 6.21 |
| Case #3 | Normal | Ectocervix | 0.55 | NA |
| | | Endocervix | NA | NA |
| | | Endometrium | 1.84 | 3.35 |
| Case #4 | Adenocarcinoma In-situ | Ectocervix | 1.16 | NA |
| | | Endocervix | 4.62 | 3.98 |
| | | Endometrium | 4.60 | 3.96 |
| Case #5 | Adenocarcinoma | Ectocervix | 0.24 | NA |
| | | Endocervix | 1.02 | 4.25 |
| | | Endometrium | 0.97 | 4.04 |
| Case #6 | Fibroid uterus | Ectocervix | 5.94 | NA |
| | | Endocervix | 8.90 | 1.50 |
| | | Endometrium | 5.60 | 0.94 |
| Case #7 | Fibroid uterus | Ectocervix | 2.71 | NA |
| | | Endocervix | 11.9 | 4.39 |
| | | Endometrium | 2.33 | 0.86 |

EXAMPLE 4

Analysis of Cancerous Cells Using Intercalating Agents

Should fluorescent reagents indicate that cells in a particular sample are cancerous, this finding can be optionally confirmed by used of an intercalating agent. Such an agent can be used to determine the ploidy of a test cell; cancerous cells are typically aneuploid.

Test cells described above were stained by the addition of 0.1 to 1 $\mu$g/ml ethidium bromide (or propidium iodide) and 0.05% Triton-X100™ non-ionic detergent. Cells were then passaged through a flow cytometer and a comparison of the results with those of cells of a normal sample indicated that the test cells were aneuploidy. This provided an independent confirmation of the results of Example 2, and a further indication that the test cells were cancerous.

EXAMPLE 5

Analysis of Activated Lymphocytes with Fluorescein Derivatives

A fluorescent reagent such as FDA is a useful measure of lymphocyte activation, both early in the course of lymphocyte activation and late. Mononuclear cells or whole blood containing lymphoid cells are activated, for example, with lectins, antibodies, superantigens, or alloantigens, by any mechanism known in the art. Activated cells are stained with a fluorescent reagent such as FDA and analyzed by flow cytometry. Stained cells can also be treated with labeled antibodies, such as Phycoerythrin-labeled antibodies to specific lymphoid subsets, to analyze the state of activity of the various subsets. The data in the Table 2 below compares various measurements of activated lymphocytes performed 3 days after activation. These values are compared with the results obtained after 7 days.

Mononuclear cells from 10 unrelated donors were activated by an alloantigen by mixing donor cells with stimulator cells at a ratio of 10:1 on day 0 and incubating the cells in RPMI medium supplemented with 2% FCS (fetal calf serum) at 37 C. T cells from these preparations were analyzed as described below at the times indicated. Blasts were quantified by making a cytospin smear of the preparation and counting the number of blasts and total number of cells after Wright-staining. Cells were also analyzed by FDA staining after 7 days. Both control unstimulated cells and activated cells were analyzed and the results below represent the percentage above control values for each mixed lymphocyte reaction. This is done because of the high variability of background activity in unstimulated donor cells. Any value at least 10% over control is considered significant. % Predictive value represents the ability of a test to predict an activated MLR (mixed lymphocyte reaction) as judged by comparing the values with blastogenesis after 1 week. Since all cultures had a large number of blasts, the % predictive value is calculated by dividing the percent of cases, showing at least 10% above control, by 100%.

This analysis demonstrates that, even on day 3, FDA staining is a better predictor of lymphocyte activation than Formazan reduction (XTT) tests or measuring CD69, a marker for lymphocyte activation. Use of XTT had a predictive value of only 60%; determining CD69 antigen expression had a predictive value of only 70%. Use of FDA had a predictive value of 80% after 3 days and 100% after 7 days. FDA is also useful for measuring lymphocyte activity after stimulation with lectins.

TABLE 2

| Allo-MLC | 3 Day XTT | 3 Day CD69 | 3 Day FDA | 7 Day FDA | % Blasts at 7 Days |
|---|---|---|---|---|---|
| 1 | 41% | 31% | 25% | 403% | 45% |
| 2 | 45% | 57% | 5% | 482% | 57% |
| 3 | 0% | 7% | 39% | 266% | 38% |
| 4 | 36% | 11% | 114% | 402% | 52% |
| 5 | 0% | 0% | 100% | 345% | 29% |
| 6 | 0% | 20% | 78% | 174% | 52% |
| 7 | 41% | 117% | 23% | 124% | 42% |
| 8 | 16% | 0% | 41% | 395% | 49% |
| 9 | 0% | 14% | 42% | 248% | 48% |
| 10 | 18% | 33% | 0% | 390% | 56% |
| Average | 19.7% | 29% | 47% | 323% | 46% |
| % Predictive Value | 60% | 70% | 80% | 100% | NA |

Figure 2:
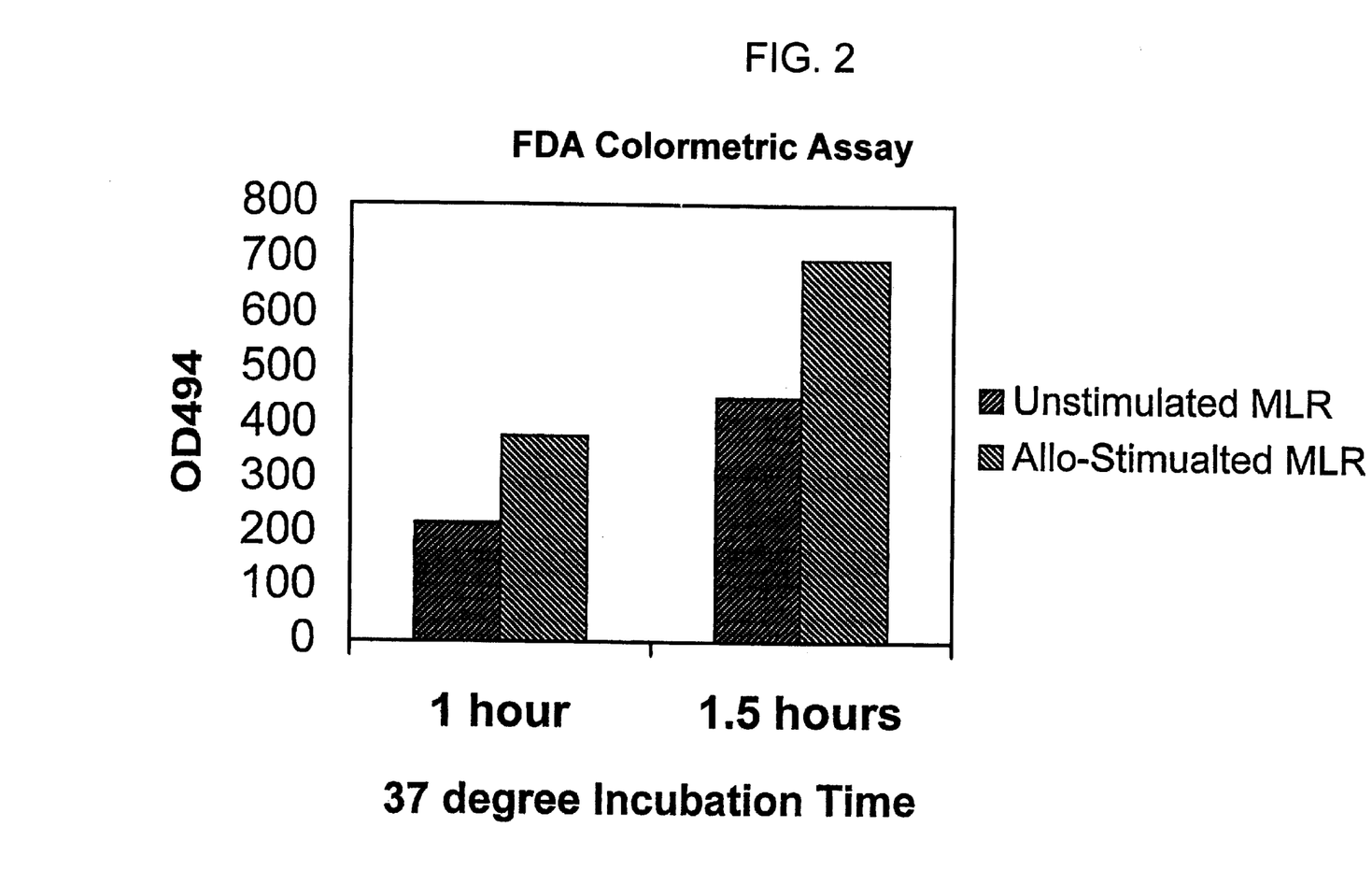
FIG. 2 is a bar graph depicting a fluorescein diacetate (FDA) calorimetric assay of unstimulated (gray bars) and allo-stimulated (solid bars) MLR.

In place of the technique described above, a colorimetric plate assay can also be performed using FDA to measure lymphocyte activation. Day 3 alloactivated cultures similar to those described above were stained with FDA for 1 or 1.5 hours in a 96-well plate. Using a colorimetric ELISA-style plate reader, an OD 494 nm could be obtained. The data are presented in FIG. 2 and indicate that, for example, after 1 hr of incubation at 37° C., unstimulated MLR demonstrated an OD494 of around 250, while allostimulated (activated) MLR had an OD of around 375. Thus, the colorimetric plate assay can be used to monitor the activation of lymphocytes.

EXAMPLE 6

Analysis of Lymphocyte Activation with Multiple Techniques, Including Use of Fluorescent Reagents Use of fluorescent reagents such as fluorescein derivatives, as described above, is an excellent indicator of lymphocyte activation and/or the presence of cancerous cells. In addition, however, other techniques may be used to verify and complement any findings obtained using fluorescein derivatives. Two tests for lymphocyte activation involve formazan reduction and expression of activation-specific markers.

Bioactivity Test Validation Report

I. Analysis of Activated Lymphocytes with Formazan Reduction Test

In order to assure that lymphocytes have been activated, a measurement of lymphocyte activation is performed on surrogate cultures, as well as on the final product, such as the cytoimplant to be used in a human patient. Bioactivity of the cultured lymphocytes is measured using a Tetrazolium (XTT) reduction assay. Levels of culture reduction capacity is compared to unstimulated cultured donor cells on day 1 through 3 of the surrogate cultures and on day 3 for the final product.

Interpretation and validation of these assays requires that each activity be compared to the appropriate unstimulated control cultures. In the case of the surrogate cultures, the activity of the allo-activated cells is compared to unactivated, cultured cells. Surrogate cultures are used so that cultures are maintained at a concentration of $0.5 \times 10^6$/mL in order to minimize the background autologous activation. Final product activity is compared to the activity of the culture on day 0.

The cells used in this culture must be from the same pheresis products used for making the cytoimplant. AIM-V medium with 2% heat inactivated donor plasma or 2% fetal calf serum is used for culture medium.

Reagents include: XTT [2,3-bis (2-methoxy-4-nitro-5-sulfo-phenyl)-2H-tetrazolium-5-carboxanalide salt], which is dissolved in sterile DPBS (Dulbecco's Phosphate Buffered Saline) at a concentration of 1 mg/mL and stored frozen protected from light; and PMS (Phenyl methane sulfonyl fluoride—a toluene sulfonyl fluoride), which is dissolved in sterile DPBS at a concentration of 1.53 mg/mL and also stored frozen protected from light. Storing this stock solution more than a month can result in crystal formation. Additional materials include: a 96-well flat-bottomed microculture plate; an ELISA plate reader capable of reading at 470 nm with reference 650 nm; and polypropylene capped sterile culture tubes.

On day 0, samples taken for cell counts and sterility tests is used to set up mock cultures as follows: 1) Donor cells alone at $0.5 \times 10^6$ cells/mL and donor+recipient cells at a ratio of 10:1 at $0.5 \times 10^6$ cells/mL from 2 to 5 mL total volume; 2) Both are placed in 10 mL polypropylene culture tubes and incubated a 37° C. in a 5–7% $CO_2$ incubator for 3 or more days; and 3) 100 µL of well-mixed culture is placed in duplicate in individual wells of 96 well plate for this assay on the first and second days. It is necessary to test the medium, donor control, and MLC to estimate the bioactivity of the MLC culture. Next, a 1 mg/mL solution of XTT fresh is made and the PMS solution thawed. PMS solution is added to XTT solution at 5 µL of PMS per mL of XTT solution, immediately before adding to the wells. (Pre-mixed reagents may cause incorrect results.) XTT/PMS (50 µL) is added per well and incubated at 37° C. for 4 hr. After this incubation, the plate is read at 470 nm reference to 650 nm in an ELISA plate reader. Average values for each culture are recorded.

In interpreting the results, duplicate values of the wells should be averaged. Background values of the medium should be subtracted to arrive at the actual value of the cultures. For example:

Average Medium Value=80 OD
Average Control Value=180 OD
Average MLC Value=230 OD
Actual Control Value=Average Control Value−Average Medium Value
Actual Control Value=(180 OD−80 OD)=100 OD The percent increase of cytoimplant values over donor alone values is calculated. The value for an MLC suitable for use in a human patient must be at least 10% above the control value. Note that the acceptable MLC Value must be >10% above the Control Value.

Acceptable MLC value=Actual Control Value+10% of Actual Control Value. For example:
Actual Control Value=100 OD
10% of Control Value=10 OD
Acceptable MLC Value≧110 OD
In this example, actual MLC Value is=150 OD (This is a culture acceptably activated for use in human patients.)

If the cytoimplant value is at least 10% above control on either day 1, 2, or 3, the cytoimplant is acceptable for human use.

Samples of frozen medium control and reconstituted frozen positive control samples should be assayed. First, medium control is thawed and 100 μL samples assayed in duplicate as described above. Next, positive control samples are thawed and diluted 100-fold with thawed control medium. 100 μL samples are assayed in duplicate as described above.

Medium control is prepared on an as-needed basis in lots of 200 individual tubes by aliquoting 500 μL of sterile RPMI medium supplemented with 2% FCS. Aliquots are frozen and held at −20° C. until needed.

Positive control samples are prepared on an as-needed basis in lots of 200 individual tubes. Human mononuclear cells not needed for cytoimplant production can be used to produce these control samples. Mononuclear cells are activated for 24 hours by incubating the cells at 37° C. in RPMI with 10% FCS supplemented with 10 μg/ML Phytohemagglutinin (PHA, Sigma) at 1×10$^6$ cells/mL. After culture, a cytospin slide stained with Diff-Quick (Baxter) can be visualized to identify the presence of lymphoblasts. If none are present, the cells are cultured for another 24 hours, or else other mononuclear cells or a different aliquot of PHA is used. If blasts are present, the cells are centrifuged at 1000×g for 10 minutes, the supernatant is replaced with 4° C. Freezing Medium at the rate of 2 mL for every 100 mL of original culture. Samples (50 μL) are aliquoted in individual tubes and freeze.

Specifications for both the medium control and the positive control samples including source of cells, amount of PHA, number of cells cultured, length of culture, and number of tubes per lot are to be recorded as part of the Lot Specifications. Both controls are to be analyzed as described above and the results are to be recorded as part of the Lot Specifications. Each Lot receives a unique alphanumeric designation, which is recorded each time the lot is used for control and validation purposes. For example:

Medium control 001
Positive control 001

This assay is accurate and linear in the range of OD 470 nm from 0.000 to 1.200 with >0.95. The reproducibility of this assay is as follows: Control tests have average %CV of 0.6% (range 0.1–2.5). Experimental values average %CV of 5.8% (range 0.8–10.0).

Correlation and Interpretive Ability: There is only a weak linear correlation with blastogenesis (r<0.9). This is due to the variable nature and kinetics of lymphocyte activation in this system. However, if MLC activation is defined as increased activity above that obtained for unstimulated control cultures at a statistically significant level, this test becomes a good predictor of activity. Statistical significance is defined as MLC values failing the null hypothesis at the 0.025 significance level using a Student's t-test (or generally at least 10% above control levels in duplicate assays, without overlapping error bars).

Positive predicative value=60% (false negatives 40%, p<0.025)
Negative predicative value=100% (false positives 0%, p<0.025)

II. Analysis of Activated Lymphocytes with Expression of CD69 by Flow Cytometry

The following protocol is derived from that of Peroni et al. (1997) *Cytometry* 27:71–6. However, any number of minor variations on this protocol are acceptable. This procedure describes the measurement of T lymphocyte activation after mixed lymphocyte alloactivation. Demonstrating lymphocyte activation before cytoimplants are released for human use is required in order to maintain a high quality of the product. Since random combinations of allogeneic mononuclear cells are being mixed and since not all combinations produce "active" MLRs, there must be some indication that activity was achieved. Activities such as CD69 expression or esterase activity that correlate with cytokine secretion can be used as surrogate measures of lymphocyte activation.

Lymphocyte activation is demonstrated by measuring increased cell surface expression of CD69 using specific fluorescently-labeled antibodies or by measuring increased intercellular esterase activity using fluorescein diacetate. Both methods can be used in conjunction with CD3-labeling using specific monoclonal antibodies labeled with a second fluorochrome. Both of these methods have been validated by comparing increased percentages of CD69-overproducing or esterase-overproducing cells with other measures of lymphocyte activation. Unstimulated lymphocytes do not express surface antigen CD69 and have only low levels of non-specific esterases. Once activated by allo-antigens or non-specific mitogens, the expression of CD69 appears within 4 to 8 hours (peak at 24) and esterase activity increases shortly after stimulation and continues for days. Not all allo-stimulated lymphocyte reactions proceed with the same kinetics. To ensure that these measures accurately reflect "activity" in all active cytoimplants, activity is measured on day 1–3 of the cultures. Small samples of donor cells alone and of the cytoimplant are incubated separately and are used to test activity.

Before mixing donor mononuclear cells with patient cells, samples of each are removed and mixed in small cultures of 3.0×10$^6$ cells/mL in 2% FCS-RPMI. These cultures are maintained at 37° C. in a 5% CO$_2$ incubator until testing.

Reagents include: Monoclonal Antibodies CD3-PE (Coulter) and CD69-FITC (Becton-Dickinson), which are kept refrigerated when not in use and protected from light. Fluorescein Diacetate (Sigma) is prepared as a stock solution in 10 mg/mL in DMSO, protected from light, and stored in frozen tested aliquots. A working solution is made weekly by diluting the stock 1:100 in DMSO, and keeping it refrigerated and protected from light. D-PBS, 0.5% paraformaldehyde-0.05% Triton-X100 in PBS.

Equipment: Flow cytometer such as an Epics XL Coulter Flow Cytometer

Quality Controls include: Internal control unstimulated and activated mononuclear cell samples are produced on an as-needed basis. Large lot-tested batches are frozen under liquid nitrogen in 250 μl aliquots in 10% DMSO freezing medium.

Mononuclear cells from normal donors are used to produce activated control specimens. Mononuclear cells from a normal donor for a given cytoimplant are often in excess and some of these cells can be used to make control samples. These cells are placed in 2% FCS-RPMI at $3.0 \times 10^6$ cell/mL up to 100 mL. Cells are cultured for 2 days at 37° C. in the presence or absence of 2 Tg/mL PHA lectin or admixed at a ratio of 10:1 with a second donor population. These calls are collected by centrifugation at 350×g for 5 minutes. The medium is removed and replaced by $\frac{1}{10}$th the volume of DMSO Freezing medium. The cells are frozen. When needed, control unstimulated and stimulated cells can be thawed quickly and resuspended at the original volume by adding nine volumes of PBS.

Control cells are analyzed to the protocol below along with cytoimplant samples. Cells are then gently vortexed and incubated 30 minutes at room temperature. 2 mL of PBS (4° C.) is added and the sample centrifuged at 1200 RPM for 10 minutes. The supernatant is decanted. 0.5 mL of 0.5% paraformaldehyde-0.05% Triton-X100 PBS is added and the solution mixed. Cells may be analyzed for fluorescence immediately or may be analyzed up to 2 weeks later if stored in a refrigerator. If RBCs are present, tubes are checked for lysis. When about 4000 cells are counted, the cytometer is stopped.

Interpreting Results: Based on previous studies, mixed lymphocyte reactions with demonstrable blastogenesis and cytokine secretion are preceded by CD69 expression or esterase activity over and above that found for unstimulated cells. Even weak MLRs demonstrate a 10% increase in CD69 or FDA over unstimulated controls. All cytoimplants testing at least 10% above unstimulated donor cells are acceptable for human use.

Example:
Donor unstimulated CD69+CD3+=2.0%
cytoimplant CD69+CD3+>2.2%

Since all MLRs are different, no direct comparison can be made between quality control values and specimen value. However, if the cytoimplant does not demonstrate activity above 110% of the control, the control is of value. If both the specimen and control showed no activity, the test should be rejected and repeated if possible. Cytoimplant specimens can be tested on days 1 and 2 of the culture. If either demonstrate activity, the cytoimplant can be released for human use.

Process Validation: Each test is accompanied by an internal control. Both medium control and pH-stimulated control mononuclear cells are available. These are processed as described above in parallel and analyzed. While the actual values may vary from test to test, the degree of stimulation over unstimulated controls should be reproducible.

On a monthly basis, lectin-activated mononuclear cells are serial diluted with equivalent numbers of unactivated cells. After analysis of these samples as described above, the plot of % activated cells versus dilution factor should produce a linear relationship.

Accuracy for this assay is significant (>4000 cells counted).

Reproducibility of this assay: Generally singlicate, previous studies show %CVs less than 2%.

Correlation and Interpretive Ability: There is only weak linear correlation with blastogenesis (r<0.9). This is due to the variable nature and kinetics of lymphocyte activation in this system. However, if MLC activation is defined as increased activity above that obtained for unstimulated control cultures at a statistically significant level, this test becomes a good predictor of activity. Statistical significance is defined as MLC values failing the null hypothesis at the, 0.025 significance level using a Student's t-test (or generally at least 10% above control levels).

Positive predicative value=70% (false negatives 30%, p<0.025)

Negative predicative value=100% (false positives 0%, p<0.025)

III. Expression of Esterase by Flow Cytometry using Fluorescein Diacetate

The methodology, accuracy and reproducibility of this assay have been described above. Correlation and Interpretive Ability: There is only weak linear correlation with blastogenesis (r<0.9). This is due to the variable nature and kinetics of lymphocyte activation in this system. However, if MLC activation is defined as increased activity above that obtained for unstimulated control cultures at a statistically significant level, this test becomes a good predictor of activity. Statistical significance is defined as MLC values failing the null hypothesis at the 0.025 significance level using a Student's t-test (or generally at least 10% above control levels).

Positive predicative value=80% (false negatives 20%, p<0.025)

Negative predicative value=100% (false positives 0%, p<0.025)

IV. Use of all three measures of lymphocyte activation combined

Three assays for testing lymphocyte activation were described in this example:
1. Formazan reduction;
2. Analysis of the level of a marker specific for lymphocyte activation, such as CD69; and
3. Use of a fluorescent reagent such as fluorescein diacetate.

The three assays can be used on the same cell sample. Each assay thus serves to confirm the results obtained with the other two assays. As above, activation is defined as activation at least 10% greater than the control unstimulated cells, tested on days 1, 2, or 3 of culture.

Correlation and Interpretive Ability: The individual positive predicative values for each assay were 60%, 70% or 80%, for the formazan reduction, CD69 level analysis, and use of fluorescein diacetate, respectively.

When used together, the Positive predicative value=100% (false negatives 0%, p<0.025)

Negative predicative value 100% (false positives 0%, p<0.025)

Although the foregoing invention has been described in some detail by way of illustration and example for purposes of clarity of understanding, it is apparent to those skilled in the art that certain changes and modifications can be practiced. Therefore, the descriptions and examples should not be construed as limiting the scope of the invention, which is delineated by the appended claims.

We claim:

1. A method for determining cancer in a human subject, comprising:
   a) obtaining ectocervix cells, and either endocervix or uterus endometrial cells from the subject;

b) adding to the cells obtained in a) an esterase substrate that can be catalyzed by esterase potentially present in the cells to form a detectable cell-associated product;

c) subsequently analyzing the cells in a device that measures the product (as distinct from the substrate in individual cells and d) correlating the ratio of product formed by the endocervix or endormetrail cells versus the product formed by the ectocervix cells with the likelihood that cells in the sample are cancerous, wherein a ratio of esterase activity in endocervix cells to ectocervix cells, or in endometrial cells to ectocervix cells, above about 4 indicates an increased likelihood that cells in the sample are cancerous.

2. The method of claim 1, which is a flow method comprising flowing the cells in suspension form through the device so as to determine esterase activity in individual cells.

3. The method of claim 2, wherein the cells are obtained from an extrafoliate sample, or any clinical fluid or solid tissue sample suspected of containing cancerous cells.

4. The method of claim 2, wherein the cells are obtained from a pap smear.

5. The method of claim 1, comprising determining the amount of product formed as a measure of esterase activity in endocervix cells and ectocervix cells from the subject, and correlating the ratio of esterase activity in the endocervix cells versus esterase activity in ectocervix cells with the likelihood that cells in the sample are cancerous.

6. The method of claim 1, comprising determining the amount of product formed by esterase activity in uterus endometrial cells and cetocervix cells from the subject, 1, and correlating the ratio of esterase activity in the endometrial cells versus esterase activity in ectocervix cells with the likelihood that cells in the sample are cancerous.

7. The method of claim 5 or 6, wherein the cancer is cervical intraepithelial neoplasia (CIN), squamous cell carcinoma, or adenocarcinoma.

8. The method of any of claims 1 to 6, further comprising measuring ploidy of cells in the sample that have an increased level of esterase activity compared with non-cancerous cells of the same tissue type, wherein presence of esterase-positive aneuploid cells in the sample is an indication or increased likelihood that cells in the sample are cancerous.

9. The method of any of claims 1 to 6, wherein the product is fluorescent, and step c) comprises measuring the fluorescence emission in each cell at a wavelength that distinguishes fluorescence of the product from fluorescence of the substrate, if any.

10. The method of claim 9, wherein the substrate is a fluorescein ester selected from the group consisting of fluorescein diacetate, carboxyfluorescein diacetate, halogenated fluorescein diacetate, carboxylated halogenated fluorescein diacetate, sulfofluorescein diacetate, azidofluorescein diacetate, fluorescein monoacetate, carboxyfluorescein monoacetate, halogenated fluorescein monoacetate, carboxylated halogenated fluorescein monoacetate, sulfofluorescein monoacetate, azidofluorescein monoacetate, and fluorescein isothiocyanate diacetate.

11. The method of claim 10, where the substrate is fluoresecin diacetate (FDA).

12. The method of any of claims 1–6, wherein the device is a fluorescence-activated flow cytometer.

13. The method of claim 1, which is a method for determining squamous cell carcinoma.

14. The method of claim 1, which is a method for determining adenocarcinoma.

* * * * *